United States Patent [19]
Therien et al.

[11] Patent Number: 5,783,306
[45] Date of Patent: Jul. 21, 1998

[54] HYPERPOLARIZABLE COMPOUNDS AND DEVICES FABRICATED THEREFROM

[75] Inventors: Michael J. Therien, Philadelphia, Pa.; Stephen G. DiMagno, Lincoln, Nebr.

[73] Assignee: Trustees of the University of Pennsylvania, Philadelphia, Pa.

[21] Appl. No.: 592,049

[22] Filed: Jan. 26, 1996

Related U.S. Application Data

[63] Continuation-in-part of Ser. No. 64,468, May 20, 1993, Pat. No. 5,493,017, which is a continuation-in-part of Ser. No. 929,943, Aug. 14, 1992, Pat. No. 5,371,199.

[51] Int. Cl.$^6$ .................. C07B 47/00; C07D 487/22; H03G 1/00; A01N 55/02
[52] U.S. Cl. .................. 428/411.1; 327/524; 427/331; 540/145; 514/185
[58] Field of Search .................. 514/185; 428/411.1, 428/332; 540/145; 534/611, 615, 11.15; 427/331; 327/524, 567

[56] References Cited

U.S. PATENT DOCUMENTS

| | | | |
|---|---|---|---|
| 5,171,741 | 12/1992 | Dougherty | 514/185 |
| 5,371,199 | 12/1994 | Therien et al. | 534/11 |
| 5,493,017 | 2/1996 | Therien et al. | 540/145 |
| 5,599,924 | 2/1997 | Therien et al. | 540/145 |

FOREIGN PATENT DOCUMENTS

| | | |
|---|---|---|
| WO 94/04614 | 3/1994 | WIPO . |
| WO 95/29916 | 11/1995 | WIPO . |

OTHER PUBLICATIONS

Boyle et al., "Iodination and Hek Alkynylation . . . " in J. Chem. Soc., Chem. Commun., p. 527, no month, 1995.
Imahori et al., "Synthesis and Properties . . . " in Bull. Chem. Soc. Jpn. 67, 2500, p. 2500, Sep. 1994.
Imahori et al., "Polyphytine–Quinone . . . " in Chem. Letters, pp. 1215–1218, no month, 1993.
DiMagno et al., "Catalytic Conversion . . . " in J. Am. Chem. Soc. 115, p. 2513, no month, 1993.
Anderson, "Meso–Alkynyl Porphyrins" in Tetrahedron Letts. vol. 33, p. 1101, no month, 1992.
Blanchard–Desce and Lehn, "Chain–length dependence of the quadratic hyperpolarizability of push–pull polyenes and carotenoids. Effect of end groups and conjugation path", Chem. Phys., 1994, (no month) 181, 281–289.
Burland, et al., "Second–Order Nonlinearity in Poled–Polymer Systems", Chem. Rev., (no month) 1994, 94, 31–75.
Cadiot and Chodkiwicz, "Couplings of Acetylenes", Chapter 9, pp. 597–647, Marcel Dekker, 1964 (no month).
Clays, et al., "Hyper–Rayleigh Scattering in Solution", Phys. Rev. Lett., (Jun.) 1991, 66, 2980–2983.
Clays, et al., "Nonlinear Optical Properties of Proteins Measured by Hyper–Rayleigh Scattering in Solution", Science, (Nov.) 1993, 262, 1419–1422.
Dehu, et al., "Donor–Acceptor Diphenylacetylenes: Geometric Structure, Electronic Structure, and Second–Order Nonlinear Optical Properties", J. Am. Chem. Soc., (no month) 1993, 115, 6198–6206.
Dhenaut, et al., "Chiral metal complexes with large octupolar optical nonlinearities", Nature, (Mar.) 1995, 374, 339–342.

(List continued on next page.)

*Primary Examiner*—John J. Zimmerman
*Assistant Examiner*—Michael LaVilla
*Attorney, Agent, or Firm*—Woodcock Washburn Kurtz Mackiewicz & Norris, LLP

[57] ABSTRACT

Substituted compounds having relatively large molecular first order hyperpolarizabilities are provided, along with devices and materials containing them. In general, the compounds bear electron-donating and electron-withdrawing chemical substituents on a polyheterocyclic core.

27 Claims, 12 Drawing Sheets

OTHER PUBLICATIONS

DiMagno, et al., "Catalytic Conversion of Simple Haloporphyrins into Alkyl–, Pyridyl–, and Vinyl–Substituted Porphyrins", *Am. Chem. Soc.*, (no month) 1993, 115, 2513–2515.

DiMagno, et al. "Facile Synthesis of meso–Tetrakis(perfluoroalkyl) porphyrins: Spectroscopic Properties and X–ray Crystal Structure of Highly Electron–Deficient 5,10,15, 20–tetrakis (heptafluoropropyl) porphyrin", *J. Org. Chem.*, (no month) 1994, 59, 6943–6948.

DiMagno, et al., "Facile Elaboration of Polphyrins via Metal–Mediated Cross–Coupling", *J. Org. Chem.*, (no month) 1994, 59, 5983–5993.

Eglinton and McCrae, "The Coupling of Acetylenic Compounds", *Adv. Org. Chem.*, (no month) 1963, 4, 225–277.

Gilmour, et al., "Synthesis of Diarylthiobarbituric Acid Chromophores with Enhanced Second–Order Optical Nonlinearities and Thermal Stability", *Chem. Mater*, (no month), 1994, 6, 1603–1604.

Laidlaw, et al., "Large second–order optical polarizabilities in mixed–valency metal complexes", *Nature*, (May) 1993, 363, 58–60.

Lin, et al., "Highly Conjugated, Acetylenyl Bridged Porphyrins: New Models for Light–Harvesting Antenna Systems", *Science*, (May) 1994, 264, 1105–1111.

Marder, et al., "Large First Hyperpolarizabilities in Push–Pull Polyenes by Tuning of the Bond Length Alternation and Aromaticity", *Science*, (Jan.) 1994, 263, 511–514.

Patai, et al., The Chemistry of Functional Groups, Supplement C, Part 1, pp. 529–534, Wiley, 1983 (no month).

Pauley and Wang, "Hyper–Rayleigh scattering studies of first order hyperpolarizability of tricyanovinylthiophene derivatives in solution", *J. Chem. Phys.*, (Apr.) 1995, 102, 6400–6405.

Peng, et al., "Large Photorefractivity in an Exceptionally Thermostable Multifunctional Polyamide", *J. Am. Chem. Soc.*, (no month) 1994, 116, 6003–6004.

Rao, et al., "Dramatically Enhanced Second–order Nonlinear Optical Susceptibilities in Tricyanovinylthiophene Derivatives", *J. Chem. Soc. Chem. Commun.*, (no month) 1993, 1118–1119.

Scamporrino, "Main–Chain Porphyrin Polymers. 1. Synthesis and Characterization of Polyethers Containing Porphyrin Units and Their Metal Derivatives", *Macromolecules*, (Mar.) 1992, 25, 1625–1632.

Sessler, et al., "A Expanded Porphyrin: The Synthesis and Structure of a New Aromatic Pentadentate Ligand", *J. Am. Chem. Soc.*, (no month) 1988, 110, 5586–5588.

Sessler, et al., "Sapphyrins and Heterosapphyrins", *Tetrahedron*, (no month) 1992, 48, 9661–9672.

Sessler, et al., "Synthesis and Characterization of Diaryl Sapphyrins Prepared under Lindsey–Type Conditions", *J. Org. Chem.*, (no month) 1995, 60, 5975–5978.

Sessler, et al., "Synthesis and Structural Studies of Sapphyrin a 22–π–Electron Pentapyrrolic Expanded Porphyrin", *J. Am. Chem. Soc.*, (no month) 1990, 112, 2810–2813.

Stiegman, et al., "The Electronic Structure and Second–Order Nonlinear Optical Properties of Donor–Acceptor Acetylenes: A Detailed Investigation of Structure–Property Relationships", *J. Am. Chem. Soc.*, (no month) 1991, 113, 4658–7666.

Terhune, et al., "Measurements of Nonlinear Light Scattering", *Phys. Rev. Lett.*, (Apr.) 1965, 14, 6861–684.

Imahori, et al., "Porphyrin–Quinone Compounds with a Spacer of Diacetylene Unit", *Chemistry Leeters*, (no month) 1993, 1215–1218.

Suslick, et al., "Push–Pull Porphyrins as Nonlinear Optical Materials", *J. Am. Chem. Soc.*, (no month) 1992, 114, 6928–6930.

LeCours, et al., "Push–Pull Arylethynyl Porphyrins: New Chromophores That Exhibit Large Molecular First–Order Hyperpolarizabilities", *J. Am. Chem. Soc.*, (no month) 1995, 118, Issue 3, pp. A–H.

1

HYPERPOLARIZABLE COMPOUNDS AND DEVICES FABRICATED THEREFROM

RELATED APPLICATION DATA

This patent application is a continuation-in-part of U.S. application Ser. No. 08/064,468, filed on May 20, 1993, now U.S. Pat. No. 5,493,017, which is a continuation-in-part of U.S. application Ser. No. 07/929,943, filed on Aug. 14, 1992, now U.S. Pat. No. 5,371,199.

GOVERNMENT SUPPORT

The research disclosed herein was supported by the National Institutes of Health (GM 48130-01A1.4) and the U.S. Department of Energy (DE-FGO2-94ER14494).

FIELD OF THE INVENTION

This invention relates to substituted polyheterocyclic compounds, to substituted compounds exhibiting relatively large molecular first order hyperpolarizabilities, and to polymers containing the compounds. This invention also relates to materials that contain the substituted polyheterocyclic compounds and are useful in the fabrication of optoelectronic devices.

BACKGROUND OF THE INVENTION

Future generations of optoelectronic devices for telecommunications, information storage, optical switching, and signal processing are predicated to a large degree on the development of materials with large nonlinear optical (NLO) responses. Toward this end, considerable effort has been directed to elucidating the chromophore design elements that correlate most closely with large first-order hyperpolarizabilities. This is due to the fact that an NLO chromophore with a high molecular first hyperpolarizability would be a highly desirable candidate for incorporation into electric field poled-polymeric systems, and thus serve as the basis for macroscopic materials for frequency doubling as well as optoelectronic devices that function as waveguide switches, modulators, filters, and polarization transformers.

Design, modification, and further fine-tuning of the magnitude of the molecular first hyperpolarizability ($\beta_{(o)}$) of a given chromophore has generally been thought of in the context of Oudar's two-state model:

$$\beta_{(0)} \propto (\mu_{ee} - \mu_{gg}) \frac{\mu_{ge}^2}{E_{ge}^2} \quad (1)$$

where g and e represent the indices of the ground and charge transfer (CT) excited states, respectively; $\mu$ is the dipole matrix element; and E is the transition energy. The very best organic chromophores for second harmonic generation that have been reported to date possess $\beta_{(o)}$'s not significantly in excess of $1,000 \times 10^{-30}$ esu. (See, Dhenaut, et al., *Nature* 1995, 374, 339; Gilmour, et al., *Chem. Mater.* 1994, 6, 1603; Blanchard-Desce, et al., *Chem. Phys.* 1994, 181, 281; and Rao, et al., *J. Chem. Soc., Chem. Commun* 1993, 1118). There exists a need for compounds exhibiting even greater molecular first order hyperpolarizability.

OBJECTS OF THE INVENTION

It is one object of the present invention to provide compounds exhibiting large molecular first order hyperpolarizabilities.

It is another object of the invention to provide optoelectronic devices fabricated from the compounds of the invention.

SUMMARY OF THE INVENTION

These and other objects are satisfied by the present invention, which provides compounds in which at least one side chain having formula $R_1$—$R_A$— and at least one side chain having formula $R_2$—$R_A$— are covalently bound to a core having formula —([MC]—[[$R_M$]$_z$—[MC]]$_m$)— wherein each [MC], independently, is a macrocycle that has a delocalized pi ($\pi$) electron system, particularly those capable of binding a metal ion. Each $R_A$, independently, is a covalent bond, alkenyl having 2 to about 20 carbon atoms, cumulenyl having 4 to about 14 carbon atoms, or alkynyl having 2 to about 10 carbon atoms, provided that at least one (and, preferably, more than one) of $R_A$ is alkenyl, cumulenyl, or alkynyl. At least one of $R_1$ and $R_2$ is an electron-donating chemical group and at least another of $R_1$ and $R_2$ is an electron-withdrawing (i.e., electron-accepting) chemical group, and each $R_M$, independently, is alkyl having 1 to about 20 carbon atoms, alkenyl having 2 to about 20 carbon atoms, cumulenyl having 4 to about 14 carbon atoms, alkynyl having 2 to about 10 carbon atoms, aryl having 3 to about 50 carbon atoms, arylalkynyl having 10 to about 24 carbon atoms, or thioether having 1 to about 10 carbon atoms. In preferred embodiments, m is 0 to about 50, and z is 0 or 1. Preferred macrocycles are porphyrins, chlorins, phorbins, benzoporphyrins, bacteriochlorins, porphyrinogens, sapphyrins, texaphyrins, and phthalocyanines. In certain embodiments, the compounds of the invention have formula:

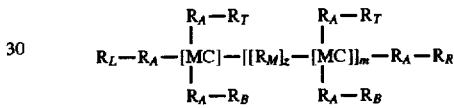

wherein [MC], $R_A$, $R_M$, m, and z are as defined above, and each $R_L$, $R_T$, $R_R$ and $R_B$ is, independently, an electron-donating group or an electron-withdrawing group, provided that at least one of $R_L$, $R_T$, $R_R$ and $R_B$ is an electron-donating group and at least one of $R_L$, $R_T$, $R_R$ and $R_B$ is an electron-withdrawing group. In preferred embodiments, one pair of $R_L$ and $R_T$, $R_L$ and $R_B$, $R_R$ and $R_T$, and $R_R$ and $R_B$ are electron-donating groups and the other pair of $R_L$ and $R_T$, $R_L$ and $R_B$, $R_R$ and $R_T$, and $R_R$ and $R_B$ are electron-withdrawing groups.

The present invention also provides materials and devices that exhibit non-linear optical effects. In general, the devices comprise a layer that contains at least one compound of the invention disposed upon a substrate. The layer can contain the compound in pure or substantially pure form or in combination with other chemical compounds such as synthetic organic polymers. In certain embodiments, for example, the layer comprises synthetic organic polymer in admixture with a compound of the invention. In other embodiments, the synthetic polymer and the compound are covalently bound.

BRIEF DESCRIPTION OF THE FIGURES

The numerous objects and advantages of the present invention can be better understood by those skilled in the art by reference to the accompanying figures, in which.

DETAILED DESCRIPTION OF THE INVENTION

Figure 1:
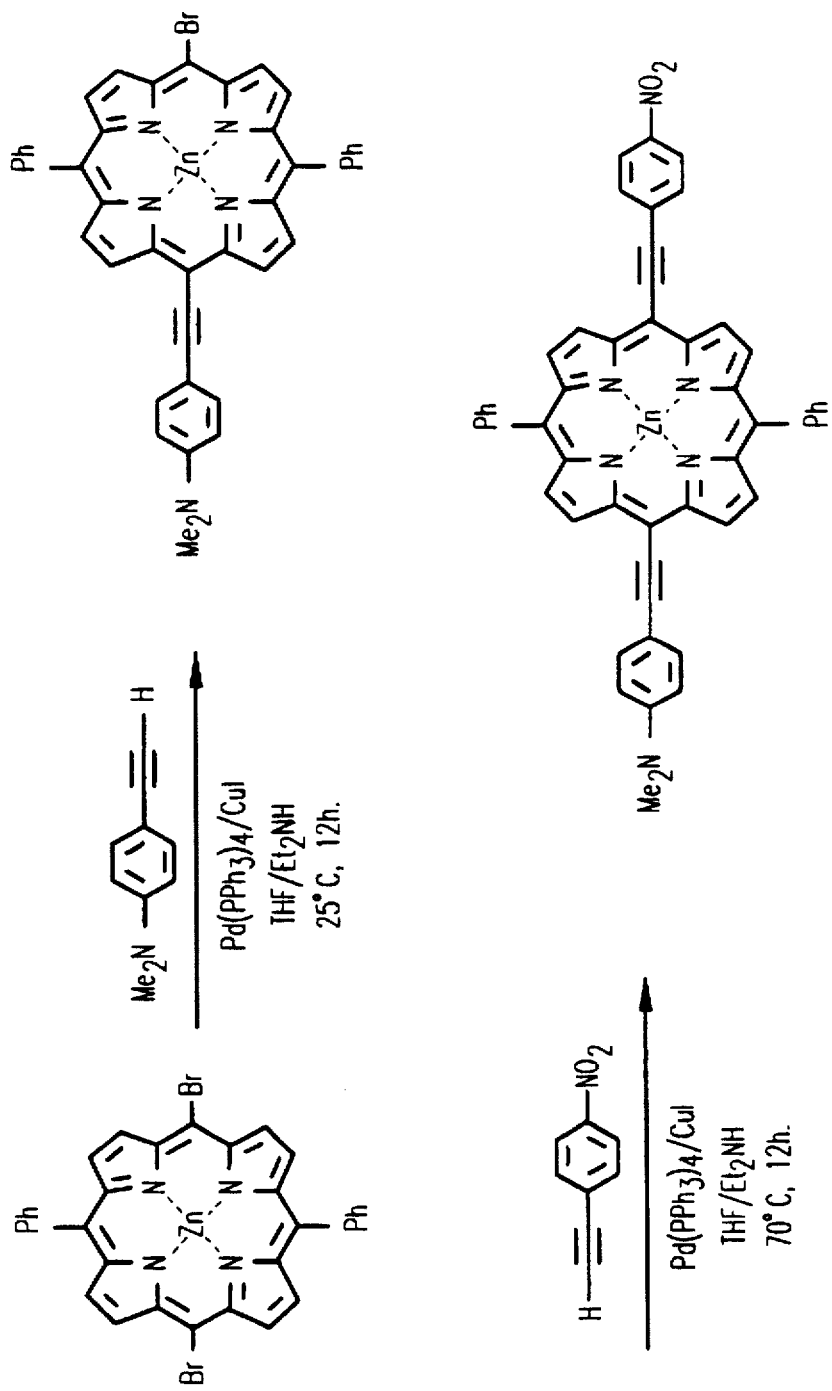
FIG. 1 is a schematic showing one means for synthesizing [5-[[4'-(dimethylamino)phenyl]ethynyl]-15-[(4"-nitrophenyl)ethynyl]-10,20-diphenylporphinato]zinc(II) ("1 (Zn$^{II}$)").

Most NLO chromophores are composed of an electron donor (D) and an electron acceptor (A), the molecular entities chiefly involved in charge redistribution, as well as a bridge (i.e., the molecular scaffolding that links the D and A portions of the chromophore). To date, the design of chromophores with good second-order nonlinear properties has focused primarily on engineering: (i) the electronic nature of the D and A, and (ii) the conjugation length of the bridge. The former controls D-A mixing with respect to a specific bridge, while the latter plays a role in modulating D-A electronic coupling and also determines the magnitude of the change in dipole moment. It is important to recognize that the parameters $\mu_{ee}-\mu_{gg}$, $\mu^2_{ge}$, and $E^2_{ge}$ in Equation (1) are all closely related. For example, increasing the bridge conjugation length generally increases the magnitude of the change of dipole moment, while concomitantly diminishing the square of the dipole matrix element and increasing the square of the CT transition energy; the latter two effects have their genesis in the fact that increased bridge lengths attenuate D-A electronic coupling. Maximizing $\beta_{(o)}$ thus involves an interplay between three parameters that do not necessarily simultaneously attain their optimal value for a particular molecular structure (D, A, bridge).

Most of the chromophores that have been studied to date for their second-order nonlinear properties can be classified as D-A systems in which the molecular bridge is either based on ethene, phenylene, ethyne, small-ring heteroaromatic, or styrene building blocks, or a combination of two or more of these simple units. Although a variety of different organic media have been utilized as D-A bridging moieties, comparatively little attention has been paid to how the details of the bridge topology and electronic structure impact the chromophore second-order NLO response, particularly when viewed alongside the body of literature describing how D-A electronic properties and bridge length modulate the molecular first hyperpolarizability.

The bridge mediated donor-acceptor electronic interaction should be large in order to maximize the strength of the transition matrix element (associated with the oscillator strength) of the charge-transfer transition. Yet, if this D-A bridge-mediated mixing is too large, the D and A states will be strongly mixed together and the molecule will lose its electronic asymmetry, that is, the difference in dipole moment between the ground and excited states. In the extreme limit where all asymmetry is lost, there is no dipole moment change between ground and excited state, so $\beta_{(o)}$ is diminished within the context of the 2-state model.

Some simple models for NLO chromophores are cast in a four orbital framework: two of these orbitals correspond to the donor- and acceptor-localized states and two to the bridge frontier orbitals. Within this four orbital description, a control parameter $\Delta$ can be defined that is approximately related to the relative orbital energies of the isolated donor (HOMO) and isolated acceptor (LUMO) orbitals ($E_D$ and $E_A$, respectively) in units of the effective coupling interaction (t') between D and A provided by the bridge.

$$\Delta=(E_D-E_A)/|t'| \qquad (2)$$

The magnitudes of $\mu_{ee}-\mu_{gg}$, $\mu^2_{ge}$, and $E^2_{ge}$ will be affected by the dimension of the parameter $\Delta$.

In an effort to construct entirely new classes of NLO chromophores with exceptional photophysical properties, we have focused on engineering bridge electronics and topology. Our most basic criterion is that the bridge should be much more polarizable than the simple polyene, polyyne, polyphenylene, and polyheteroaromatic structures that have been most commonly used. Ideally, the bridge-localized excited state should dramatically alter D-A electronic coupling relative to the coupling the ground-state bridge provides.

One approach to enabling such differential ground- and excited-state coupling is to choose a D-A bridging motif that is capable of accessing a resonance form in its excited state that is unattainable for the ground-state structure. Such an excited-state resonance structure would be optimal if it produced a large transition dipole oriented directly along the D-to-A molecular charge transfer axis. A designed excited state with these properties would facilitate large molecular first hyperpolarizabilities since the magnitude of the change in dipole moment would not be held ransom by significant diminution of the oscillator strength of the CT transition or an increase in the transition energy at relatively large D-A distances, since a high oscillator strength, bridge-centered transition would now directly couple D to A. Presumably, if the orientation and dipolar nature of the bridge-centered CT transition could be maintained over a long range in such a system, $\mu_{ee}-\mu_{gg}$ and $\mu^2_{ge}$ would simultaneously increase with augmented bridge lengths while concomitantly maintaining or slightly reducing $E^2_{ge}$.

It has been found in accordance with the present invention that these desirable design elements for NLO chromophores preferably are embodied by compounds having formula:

wherein:

each [MC], independently, is a porphyrin, chlorin, phorbin, benzoporphyrin, bacteriochlorin, porphyrinogen, sapphyrin, texaphyrin, or phthalocyanine;

each $R_A$, independently, is a covalent bond, alkenyl having 2 to about 20 carbon atoms, cumulenyl having 4 to about 14 carbon atoms, or alkynyl having 2 to about 10 carbon atoms, provided that at least one (and, preferably, more than one) of $R_A$ is alkenyl, cumulenyl, or alkynyl;

each $R_M$, independently, is alkyl having 1 to about 20 carbon atoms, alkenyl having 2 to about 20 carbon atoms, cumulenyl having 4 to about 14 carbon atoms, alkynyl having 2 to about 10 carbon atoms, aryl having 3 to about 50 carbon atoms, arylalkynyl having 10 to about 24 carbon atoms, or thioether having 1 to about 10 carbon atoms;

one of $R_1$ and $R_2$ is a chemical group that is electron-donating;

the other of $R_1$ and $R_2$ is a chemical group that is electron-withdrawing;

m is 0 to about 50; and z is 0 or 1.

In certain embodiments, the compounds of the invention have formula:

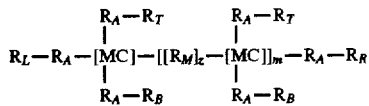

wherein each $R_L$, $R_T$, $R_R$ and $R_B$ is, independently, an electron-donating group or an electron-withdrawing group, provided that at least one of $R_L$, $R_T$, $R_R$ and $R_B$ is an electron-donating group and at least one of $R_L$, $R_T$, $R_R$ and $R_B$ is an electron-withdrawing group. In preferred embodiments, one pair of $R_L$ and $R_T$, $R_L$ and $R_B$, $R_R$ and $R_T$, or $R_R$ and $R_B$ are electron-donating groups and the other pair of $R_L$ and $R_T$, $R_L$ and $R_B$, $R_R$ and $R_T$, and $R_R$ and $R_B$ are electron-withdrawing groups.

Virtually any covalent linking group known in the art can be used as $R_M$ in accordance with the present invention to link [MC] groups, including simple covalent bonds, alkyl groups having 1 to about 20 carbon atoms, alkenyl groups having 2 to about 20 carbon atoms, cumulenyl groups having 4 to about 14 carbon atoms, alkynyl groups having 2 to about 10 carbon atoms, aryl groups having 3 to about 50 carbon atoms, arylalkynyl groups having 10 to about 24 carbon atoms, and thioethers having 1 to about 10 carbon atoms. These linking groups can be attached to any of the available [MC] ring positions. Porphyrins, for example, have 12 available attachment positions. Also, as will be recognized, one or more of the [MC] ring positions not bearing $R_A$, $R_M$, $R_1$, $R_2$, or [MC] groups can bear other types of substituents, such as phenyl and haloalkyl groups.

Alkyl groups according to the invention are aliphatic and substituted aliphatic groups having from 1 to about 10 carbon atoms, including methyl, ethyl, and tert-butyl groups. Aryl groups are aromatic and substituted aromatic groups having 3 to about 50 carbon atoms (preferably 6 to about 50 carbon atoms), including phenyl, benzyl, and imidazole groups. Cumulenyl groups are those having adjacent (or cumulative) carbon-carbon double bonds, preferably those having 4 to about 14 carbon atoms. Alkenyl groups are substituted and unsubstituted groups having 2 to about 20 carbon atoms and one or more carbon-carbon double bond, including ethenyl and butadienyl groups. Alkynyl groups are substituted and unsubstituted groups having 2 to about 10 carbon atoms and one or more carbon-carbon triple bond, including ethynyl butadiynyl groups. Arylalkynyl groups are substituted and unsubstituted groups having 10 to about 24 carbon atoms and covalently bound aryl and alkynyl portions, such as diethynylbenzene groups. Thioethers are compounds having 1 to about 10 carbon atoms and the general formula —S—(alkyl) or —S—(alkyl)—.

Preferred compounds of the invention have formula (1) or (2):

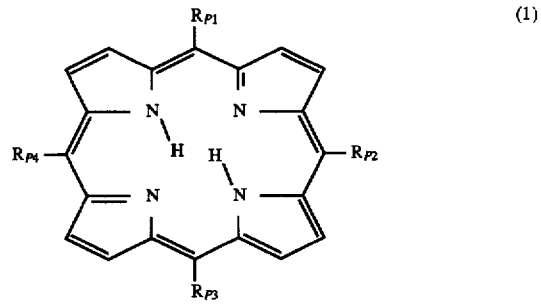

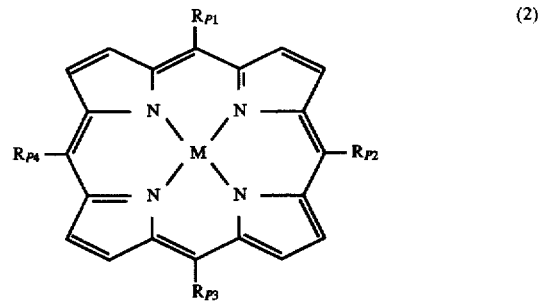

wherein M is a metal atom, $R_{P4}$ is —$R_A$—$R_L$, $R_{P2}$ is —$R_A$—$R_R$, $R_{P1}$ is —$R_A$—$R_T$ or aryl having 3 to about 60 carbon atoms, $R_{P3}$ is —$R_A$—$R_B$ or aryl having 3 to about 60 carbon atoms, and $R_A$ is cumulenyl, polyenyl, or polyynyl, preferably ethenyl, butadienyl, substituted butadienyl, ethynyl, or butadiynyl. In certain embodiments, one or more of the $R_{P1}$—$R_{P4}$ groups are positioned at pyrrolic porphyrin positions. In certain embodiments, compounds of the invention have formulas (3) and (4):

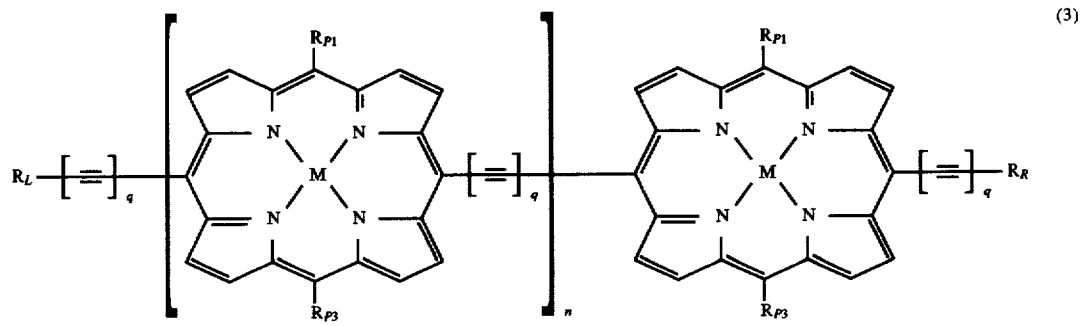

-continued

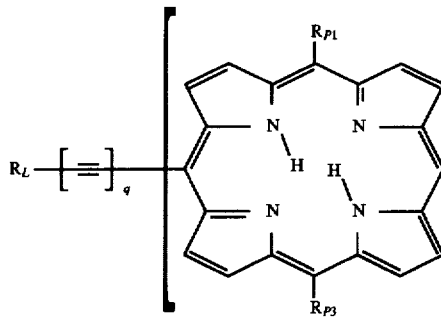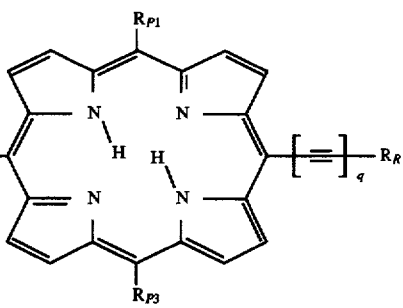

(4)

wherein q is 1–5 (preferably 1–2) and n is 0–50 (preferably 0–10). Further representative compounds of the invention are shown in FIGS. 7–10, wherein $R_L$ and $R_B$ are electron-donating groups. $R_T$ and $R_R$ are electron-withdrawing groups, and Ph is phenyl.

Those skilled in the art will recognize that porphyrins are derivatives of porphine, a conjugated cyclic structure of four pyrrole rings linked through their 2- and 5-positions by methine bridges. Porphyrins can bear up to 12 substituents at meso (i.e., α) and pyrrolic (i.e., β) positions thereof. (See, e.g., U.S. Pat. No. 5,371,199, which is incorporated by reference). As used herein, opposite meso positions are the 5 and 15 positions and 10 and 20 positions. Related heteroatom-containing compounds such as chlorins, phorbins, benzoporphyrins, bacteriochlorins, porphyrinogens, sapphyrins, texaphyrins, and pthalocyanines are well known in the art. see, e.g., Dolphin, ed., The Porphyrins, New York, Academic Press, 1978; Sessler, et al., J. Am. Chem. Soc. 1988, 110, 5586; Sessler, et al., Tetrahedron 1992, 48, 9661; Sessler, et al., J. Org. Chem. 1995, 60, 5975; Sessler, et al., J. Am. Chem. Soc. 1990, 112, 2810; Zollinger, Color Chemistry, New York, VCH Publishers, 1991, Okawara, et al., Organic Colorants, New York, Elsevier, 1988, and Kaeda, Laser Dyes, New York, Academic Press, 1984.

$R_1$ and $R_2$ (and, in turn, $R_L$, $R_R$, $R_T$, and $R_B$) can be any of a wide variety of chemical functional groups. Numerous examples of electron-donating and electron-withdrawing groups are well-known to those skilled in the art. (See, e.g., Gordon, et al., The Chemist's Companion, New York, John Wiley & Sons, 1972). Further, electron-donating and electron-withdrawing groups can be identified through routine experimentation by, for example, substitution in a molecule and testing of any resultant inductive effects. Representative electron-donating groups include appropriately-substituted alkyl and aryl groups, alkylamino groups, arylamino groups, $NH_2$, alkoxy groups, OH, alkylthio groups, SH, —OC(O)—(alkyl), cycloheptatrienes, and heterocycles such as julolidinyl groups. (See, e.g., Marder, et al., Science 1994, 263, 511). Representative electron-withdrawing groups include appropriately-substituted alkyl and aryl groups (such as haloalkyl groups), $N-(alkyl)_3^+$, $S-(alkyl)_2^+$, $NH_3^+$, $NO_2$, $SO_2-(alkyl)$, CN, $SO_2-(aryl)$, C(O)OH, F, Cl, Br, I, cyclopentadienyl, C(O)O-(alkyl), C(O)-(alkyl), CHO, and heterocycles such as N,N'-diethylthiobarbituric acid, 3-phenyl-5-isoxazolone, quinone, 4-pyridyl, and 3-pyridyl groups. Preferred groups are alkyl groups that are electron-donating relative to hydrogen, aryl groups that are electron-donating relative to hydrogen, alkyl groups that are electron-withdrawing relative to hydrogen, and aryl groups that are electron-withdrawing relative to hydrogen. Particularly preferred are aromatic hydrocarbons bearing at least one substituent that is electron-donating relative to hydrogen, heterocycles bearing at least one substituent that is electron-donating relative to hydrogen, aromatic hydrocarbons bearing at least one substituent that is electron-withdrawing relative to hydrogen, and heterocycles bearing at least one substituent that is electron-withdrawing relative to hydrogen. Preferred compounds are those in which at least one electron-donating group is not an alkyl group. Particularly preferred among such compounds are those in which at least one electron-donating group is not an alkyl group and at least one electron-withdrawing group is not a quinone or an alkylene quinone. Even more preferred among such compounds are those wherein [MC] is not a porphyrin, particularly compounds wherein $R_A$ is not alkynyl.

The electron-donating substituent preferably is an alkyl group, an alkylamino group, an arylamino group, $NH_2$, an alkoxyl group, OH, an alkylthio group, SH, or —OC(O)-(alkyl), and the electron-withdrawing substituent preferably is $N-(alkyl)_3^+$, $S-(alkyl)_2^+$, $NH_3^+$, $NO_2$, $SO_2-(alkyl)$, CN, $SO_2-(aryl)$, C(O)OH, F, Cl, Br, I, C(O)O-(alkyl), C(O)-(alkyl) or CHO. Particularly preferred electron-donating substituents include alkylamino and arylamino groups such as 4-dimethylaminophenyl and 4-diarylaminophenyl groups. Particularly preferred electron-withdrawing substituents include $NO_2$, CN, quinone, and pyridinium groups.

M in, for example, formula (3) can be the same or different and can be a lanthanide or actinide or a metal such as Sc, Ti, V, Cr, Mn, Fe, Co, Ni, Cu, Y, Zr, Nb, Mo, Ru, Rh, Pd, Ag, La, Hf, Ta, W, Re, Os, Ir, Pt, Cd, Hg, Li or Au.

The compounds of the invention can be prepared by a variety of techniques, including metal-mediated cross-coupling techniques (See, e.g., U.S. Pat. No. 5,371,199 (Therien, et al.; incorporated herein by reference); International Patent Application WO 94/04614 (Therien, et al.); DiMagno, et al., J. Am. Chem. Soc. 1993, 115, 2513; DiMagno, et al., J. Org. Chem. 1993, 58, 5983; and Lin, et al., Science 1994, 264, 1105) and condensation techniques (See, e.g., International Patent Application PCT/US95/05180, filed Apr. 26, 1995, and DiMagno, et al., J. Org. Chem. 1994, 59, 6943). The compounds of the invention generally can be prepared by modifying these techniques for use with appropriate starting materials. FIG. 1, for example, shows one synthesis for [5-[[4'-(dimethylamino)phenyl]ethynyl]-15-[(4"-nitrophenyl)ethynyl]-10,20-diphenylporphinato]zinc(II) ("1(Zn$^{II}$)"), discussed in greater detail in Examples 1 and 2.

Figure 2:
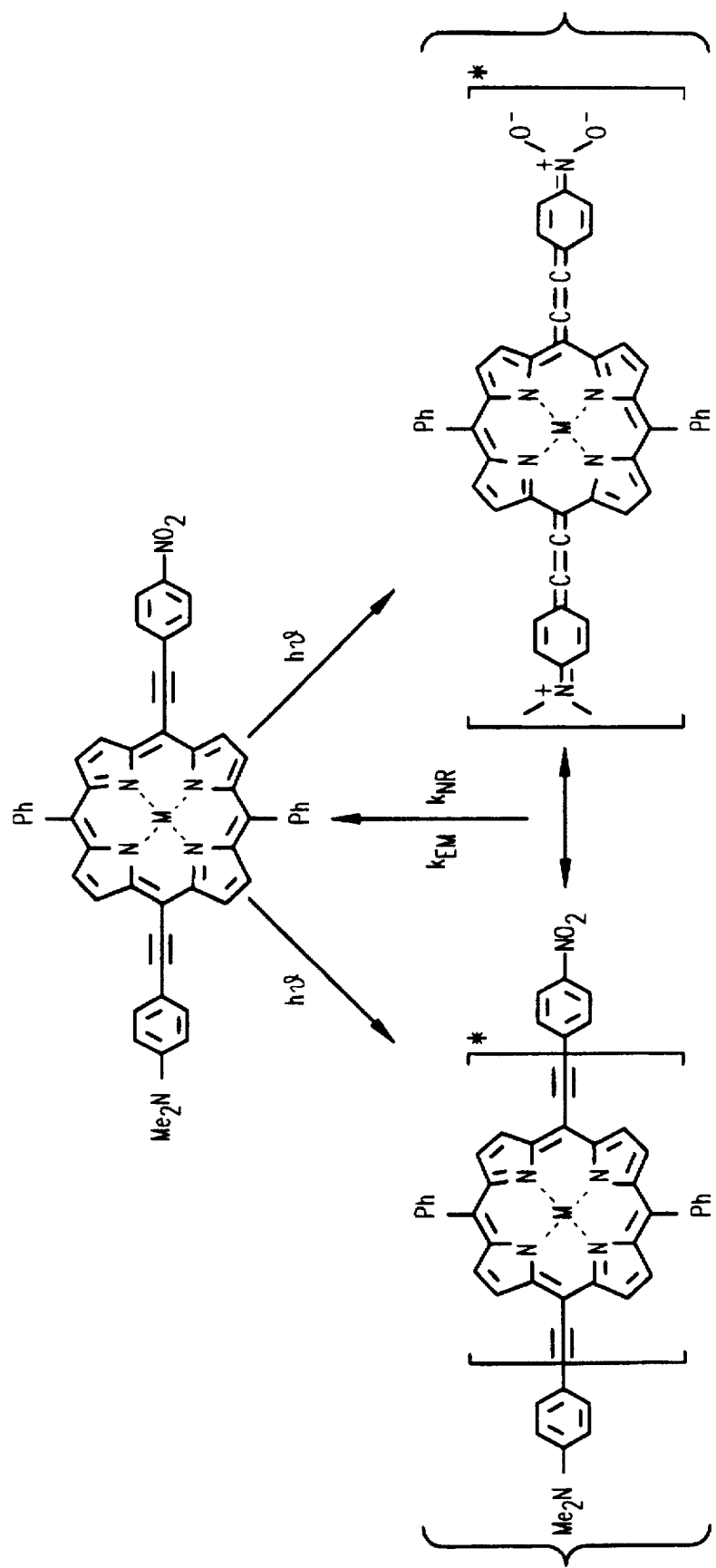
FIG. 2 is a schematic showing a proposed excited state for [5-[[4'-(dimethylamino)phenyl]ethynyl]-15-[(4"-nitrophenyl)ethynyl]-10,20-diphenylporphinato]zinc(II) ("1 (Zn$^{II}$)*").

Photophysical studies of 1(Zn$^{II}$) show that it possesses a host of unusual optical properties. For example, resonance Raman studies indicate that the excited states of [5-(4'-dimethylaminophenylethynyl)-15-(4"-nitrophenylethynyl) 10,20-diphenylporphinato]metal complexes exhibit reduced bond order in the ethynyl groups as well as in the 4'-dimethylaminophenyl and 4"-nitrophenyl aryl rings with respect to that seen in their ground-state spectra. Downshifting of these vibrational frequencies is not observed when the excited-state resonance Raman spectrum is compared with the analogous ground-state spectra for the corresponding symmetrically-substituted 5,15-bis(arylethynyl)-10,20-diphenylporphinato]metal species. While not wishing to be bound by any particular theory, FIG. 2 summarizes this data and presents our current picture of the excited state of [5-[[4'-(dimethylamino)phenyl]ethynyl]-15-[(4"-nitrophenyl)ethynyl]-10,20-diphenylporphinato]zinc(II), $1(Zn^{II})^*$. Note that $1(Zn^{II})^*$ can access a cumulenic resonance form while $1(Zn^{II})$ is best described as a supramolecular chromophore in which three aromatic ring systems are linked by ordinary carbon-carbon single and triple bonds.

The compounds of the present invention generally exhibit relatively large molecular first hyperpolarizabilities, as measured using the hyper-Rayleigh (light) scattering (HRS) technique (See, Pauley, et al., *J. Chem. Phys.* 1995, 102, 6400), see also, Terhune, et al., *Phys. Rev. Lett.* 1965, 14, 681; Clays, et al., *Phys. Rev. Lett.* 1991, 66, 2980; Clays, et al., *Science* 1993, 262, 14192; Laidlaw, et al., *Nature* 1993, 363, 58; and Pauley, et al., *J. Chem. Phys.* 1995, 102, 6400). Compounds with relatively large hyperpolarizabilities are those having β values greater than $500 \times 10^{-30}$ esu at 1906 nm or 1064 nm incident radiation. Normally, the first order nonlinear effect is absent in an isotropic medium because of the centrosymmetric environment. Molecular first hyperpolarizabilities are measured by the electric field-induced second harmonic generation (EFISH) and hyper-Rayleigh (light) scattering (HRS) techniques. The HRS technique is very sensitive to solution concentration. It is thus an ideal method for the evaluation of the hyperpolarizabilities of the high extinction coefficient chromophores of the invention.

Figure 3A:
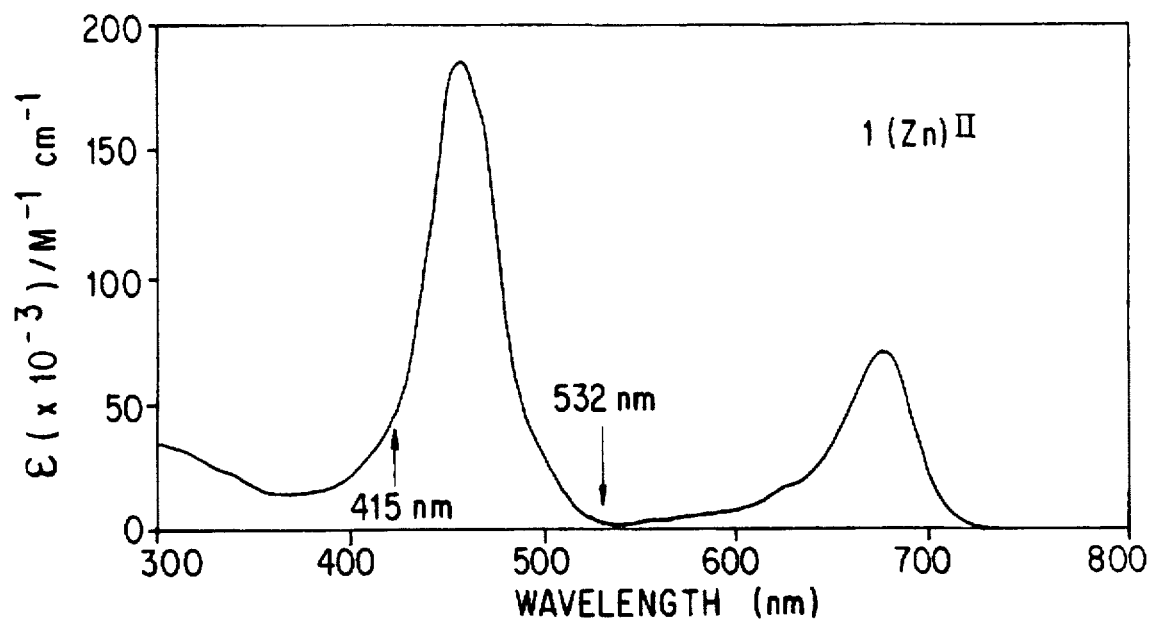
FIG. 3 shows electronic spectra of [1(Zn$^{II}$)] and [5-[[4'-(dimethylamino)phenyl]ethynyl]-15-[(4"-nitrophenyl)ethynyl]-10,20-diphenylporphinato]copper(II) ("1(Cu$^{II}$)") recorded in chloroform.
Figure 3B:
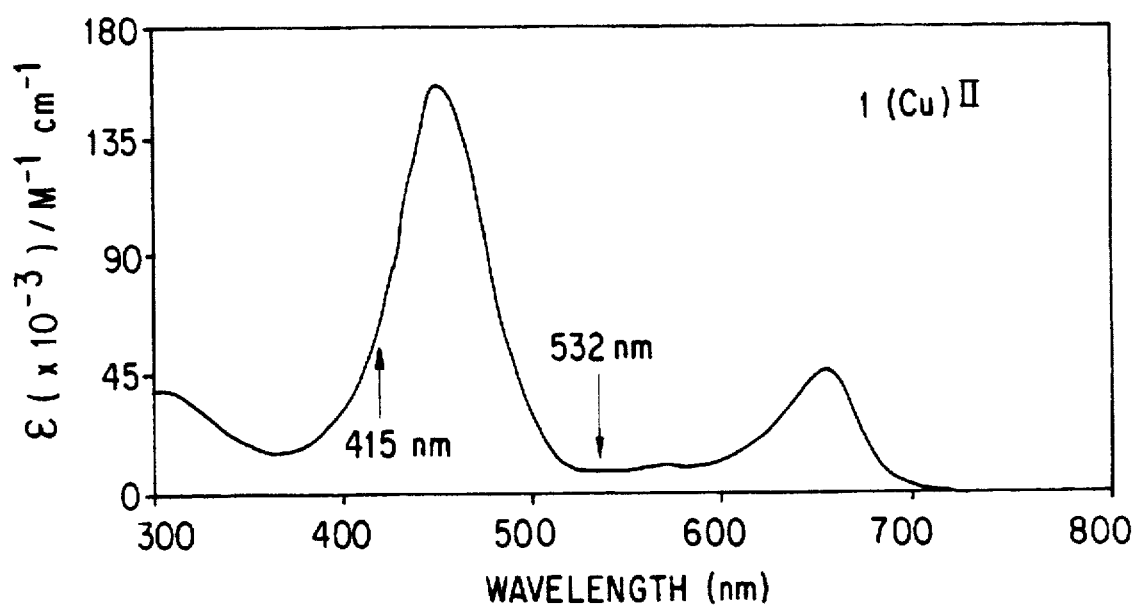

As discussed in greater detail in Example 8, measurements of the molecular first hyperpolarizability for both $1(Zn^{II})$ and $1(Cu^{II})$ were carried out in chloroform solvent for incident irradiation wavelengths of 830 ($\lambda_1$) and 1064 ($\lambda_2$) nm. FIG. 3 shows the electronic absorption spectra of $1(Zn^{II})$ and $1(Cu^{II})$. Note that the scattered light at the second harmonic of 830 nm (0.5 $\lambda_1$) will be partially absorbed by both chromophores on the blue shoulder of the Soret transition, while scattered light of wavelength 532 nm (0.5 $\lambda_2$) corresponds to a frequency in the optically-transparent region of the spectra of both $1(Zn^{II})$ and $1(Cu^{II})$. HRS data obtained at incident irradiation wavelength $\lambda_1$ were Beer's Law-corrected for chromophore absorption to eliminate the effective signal attenuation prior to calculating $\beta_{830}$ using an approach described by Pauley, et al., *J. Chem. Phys.* 1995, 102, 6400.

Figure 4A:
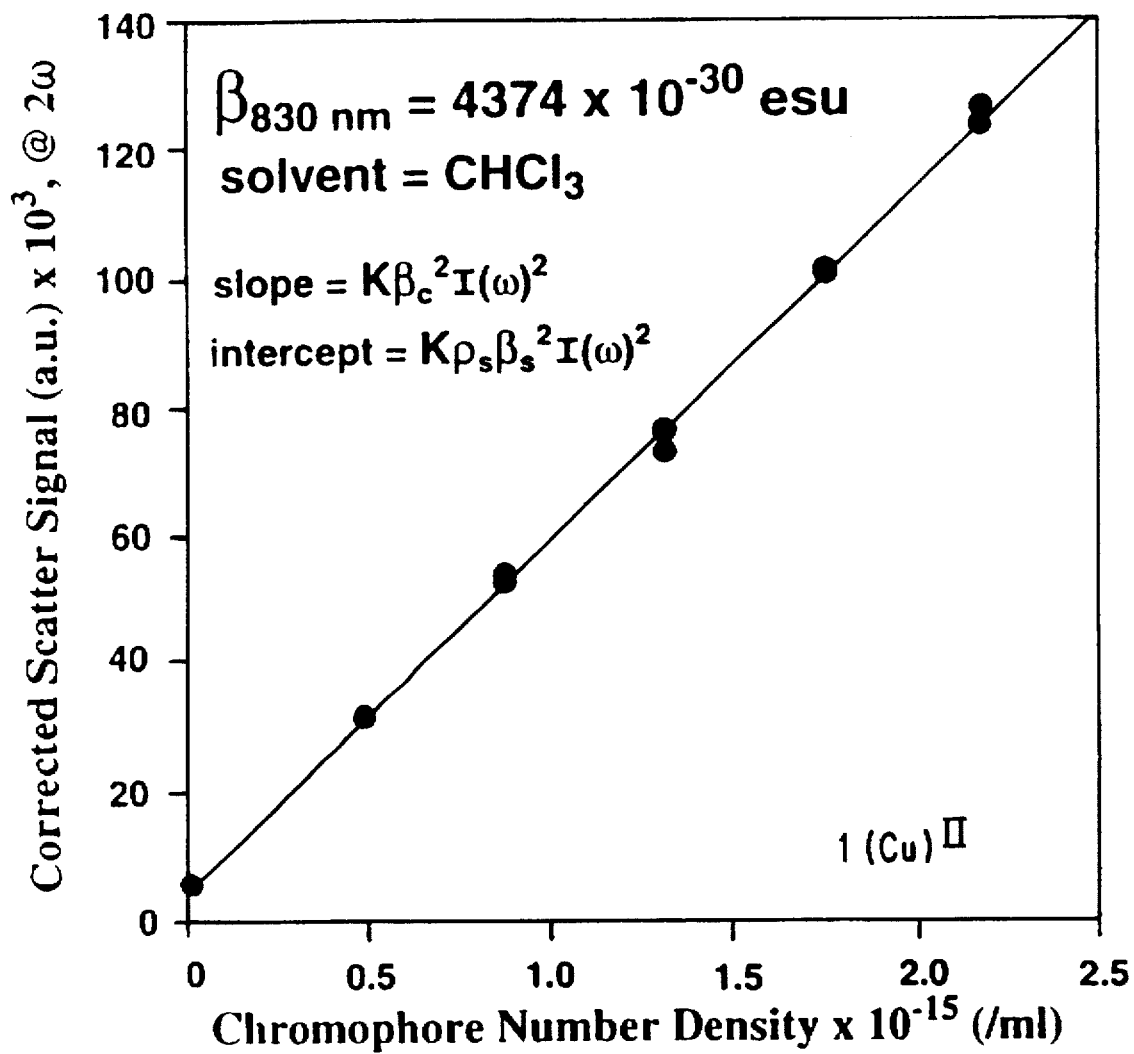
FIGS. 4 and 5 show plots of hyper-Rayleigh scattering signal (corrected for absorption) vs. chromophore number density for 1(Cu$^{II}$) and 1(Zn$^{II}$) in chloroform at irradiation wavelengths of 830 nm and 1064 nm, respectively.
Figure 4B:
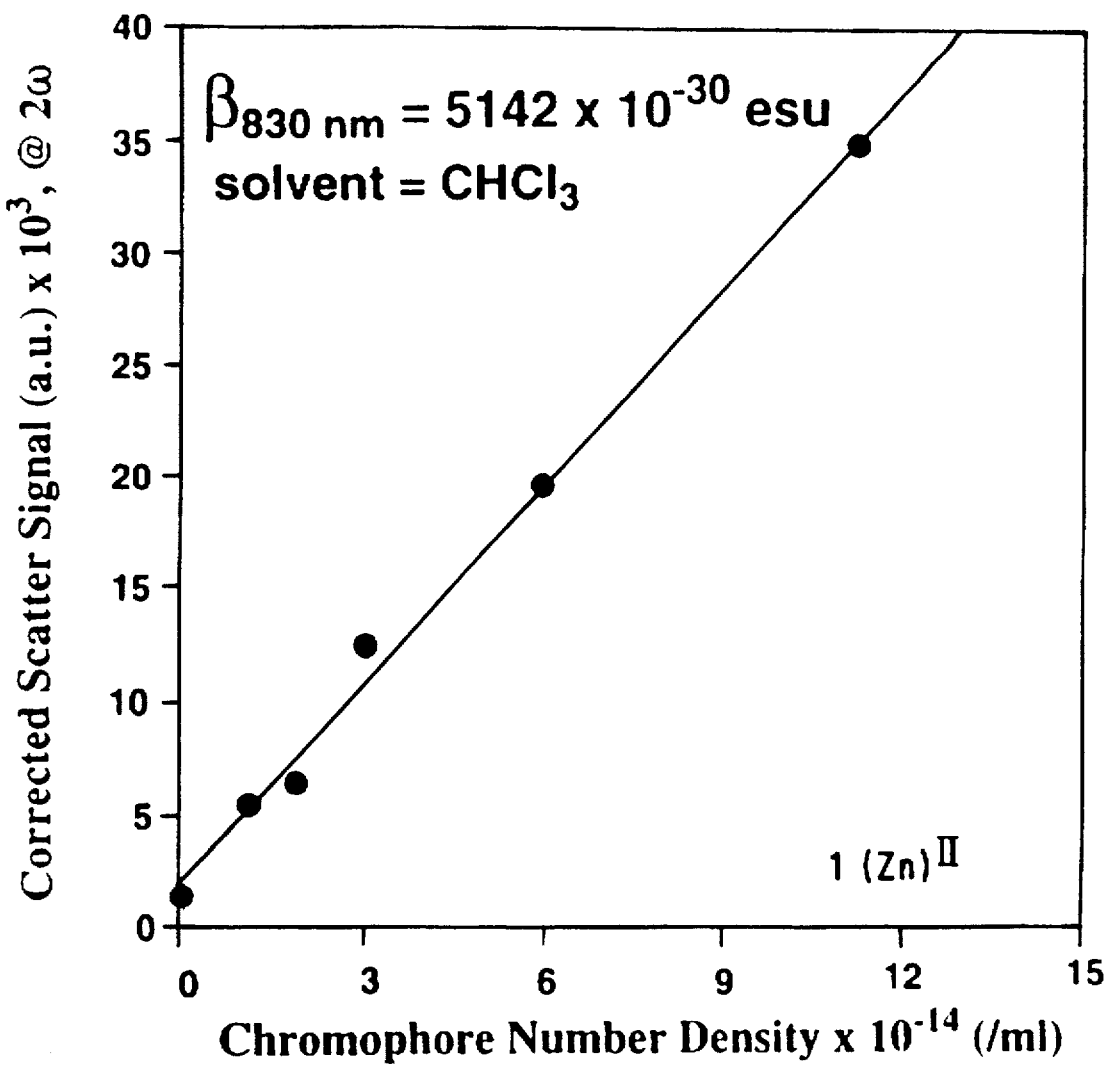
Figure 5A:
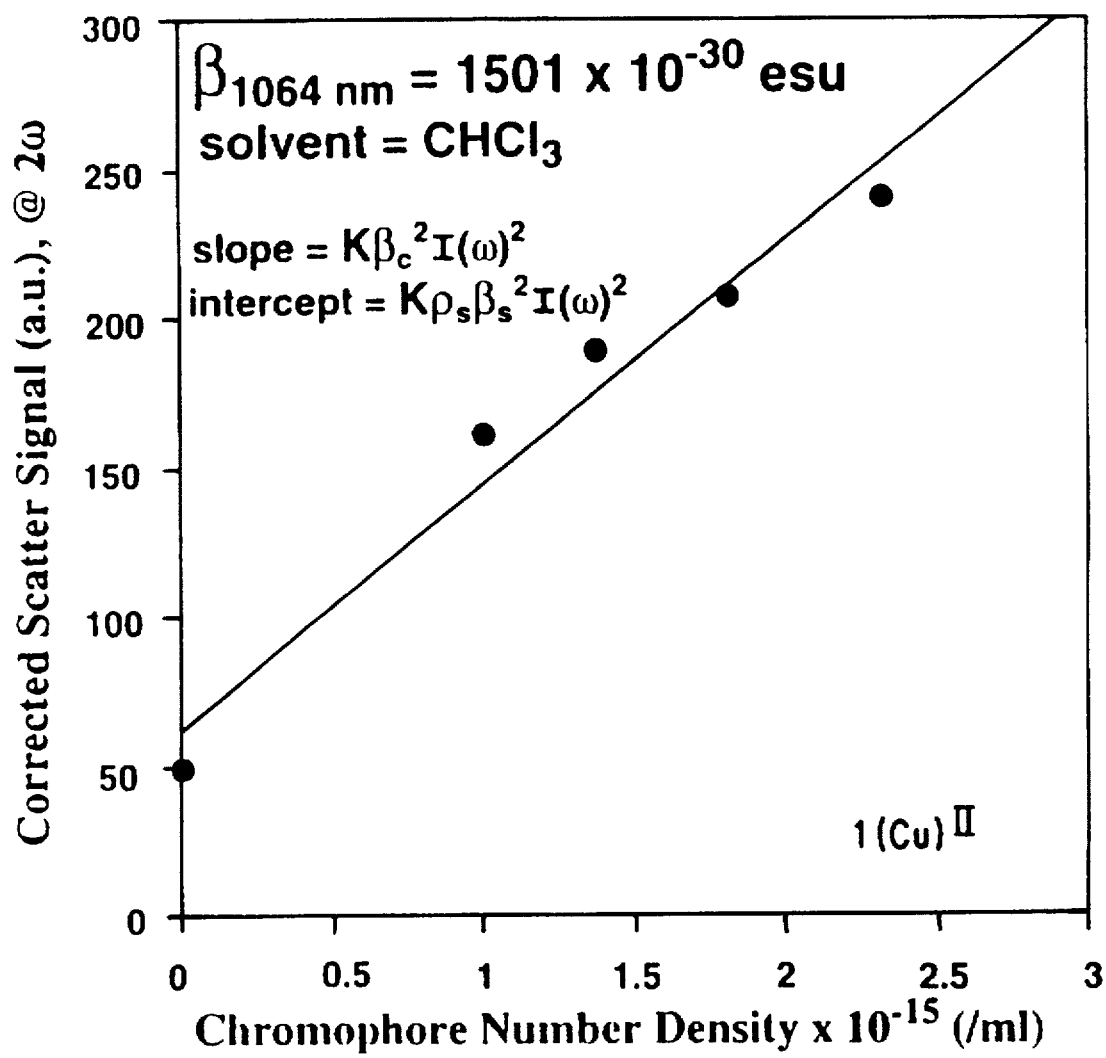
Figure 5B:
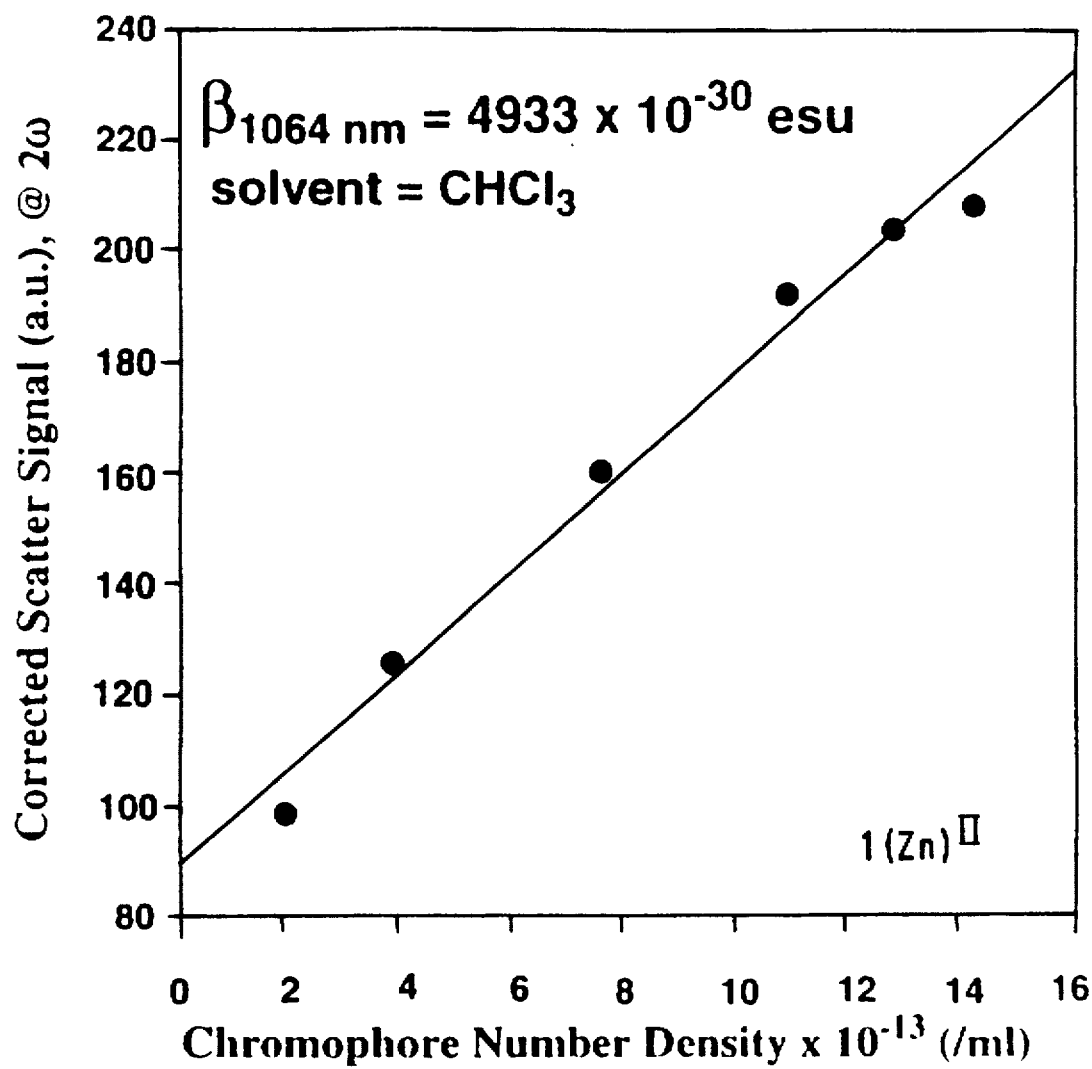

The total scattered light intensity at 0.5 λ (2ω) is given by:

$$I(2\omega)=K(\rho_s\beta_s^2+\rho_c\beta_c^2)I(\omega)^2 \qquad (3)$$

where ρS and ρC are the number densities of solvent and chromophore molecules, $\beta_s$ and $\beta_c$ the major hyperpolarizability tensor of the solvent and chromophore, ω the frequency of incident irradiation, 2ω the second harmonic frequency, I the light intensity, and K a quantity determined only by the scattering geometry and local field factors at low chromophore concentrations. FIGS. 4 and 5 plot the hyper Rayleigh scattering signal at I(2ω) versus chromophore number density for $1(Zn^{II})$ and $1(Cu^{II})$ in chloroform solvent in the very dilute concentration regime for irradiation at wavelengths $\lambda_1$ and $\lambda_2$. $\beta_{830}$ and $\beta_{1064}$ for both chromophores can be directly evaluated from these plots. Non-negative intercepts were obtained in all cases at low chromophore concentrations. The quadratic dependence of I(2ω) on I(ω) verified that the scattered light intensity clearly arises from the nonlinear hyper-Rayleigh scattering process. Chromophore molecular first hyperpolarizabilities were referenced internally against the known solvent β value, and the well-studied NLO chromophore p-nitroaniline (PNA) was used as an external reference in these experiments. Consistent β values were obtained irrespective of the choice of reference.

The β values evaluated from the data presented in FIGS. 3 and 4 are exceptionally large. The wavelength dependence of the molecular first hyperpolarizability for $1(Cu^{II})$ shows that changing the incident irradiation wavelength from 830 to 1064 nm results in a decrease in the magnitude of the evaluated β by approximately 65 percent ($\beta_{830}$=4374×10$^{-30}$ esu; $\beta_{1064}$=1501×10$^{-30}$ esu). In contrast to that seen for $1(Cu^{II})$, the measured β value for $1(Zn^{II})$ in chloroform appears to be virtually independent of irradiation wavelength ($\beta_{830}$=5142×10$^{-30}$ esu; $\beta_{1064}$=4933×10$^{-30}$ esu).

Although theoretical studies based on INDO/SCI calculations within a sum over states formalism are consistent with the very large, experimentally determined molecular first hyperpolarizabilities of the compounds of the invention, they do not account for the observed frequency dependence of β for these compounds. These studies estimate that $\beta_{1064}$ for $1(Zn^{II})$ should be approximately three to six fold enhanced with respect to $\beta_{(o)}$, the molecular first hyperpolarizability at zero frequency. Such a diminution of $\beta_{(o)}$ with respect to $\beta_{1064}$ may be may overestimated, given that theory predicts $\beta_{830}$ to be much greater than $\beta_{1064}$, and that the mode of resonant enhancement predicted to be important for$1(Zn^{II})$ in these calculations is not expected to be experimentally significant. Nevertheless, a conservatively estimated minimal magnitude of $\beta_{(o)}$ for this chromophore of approximately 800×10$^{-30}$ esu compares well with the extrapolated $\beta_{(o)}$'s for the very best organic chromophores for second harmonic generation reported to date. These molecules possess $\beta_{(o)}$'s not significantly in excess of 1,000×10$^{-30}$ esu. As such, $1(Zn^{II})$ represents the first metal-containing chromophore with a molecular first hyperpolarizability in this range. Moreover, because $1(Zn^{II})$ possesses a significant dipole moment (about 12.3 D), the technologically relevant parameter $\mu\beta_{(o)}$ will also be correspondingly large. It is worthy of note that this extrapolated $\beta_{(o)}$ value for $1(Zn^{II})$ is more than twenty-fold greater than the molecular first hyperpolarizabilities that have been evaluated for the simple diarylethynes (see, Stiegman, et al., *J. Am. Chem. Soc.* 1991, 113, 7658 and Dehu, et al., *J. Am. Chem. Soc.* 1993, 115, 6198), demonstrating the degree of enhancement in $\beta_{(o)}$ values that can be achieved using the compounds of the invention. Moreover, the thermal stabilities of porphyrins are outstanding and greatly exceed that of the polymer matrices thought to be ideal for electrooptical applications (See, e.g, Peng, et al., *J. Am. Chem. Soc.* 1994, 116, 6003 and Scamporrino, et al., *Macromolecules* 1992, 25, 1625). For example, thermogravimetric analysis of $1(Zn^{II})$ and $1(Cu^{++})$ demonstrate that they are stable to prolonged heating (in excess of 200° C.) both in the solid state and in polyimide thin films. The concepts for chromophore engineering discussed herein should find wide application in the field of nonlinear optics.

Figure 6:
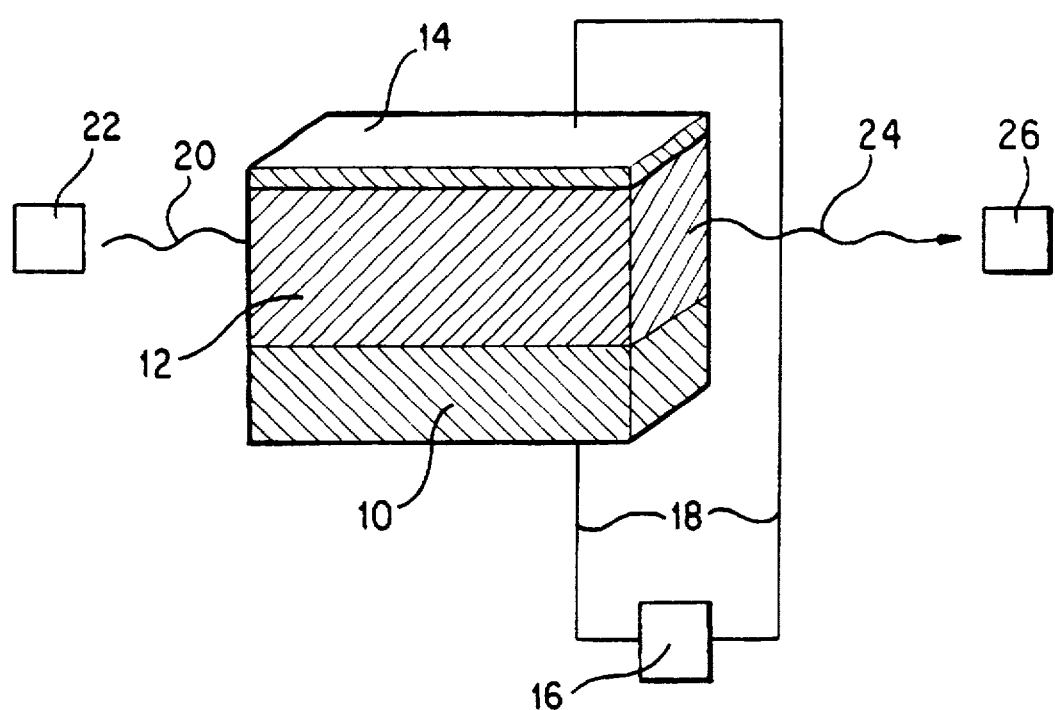
FIG. 6 shows a device according to the invention comprising a substrate and a layer that contains a compound of the invention.
Figure 7:
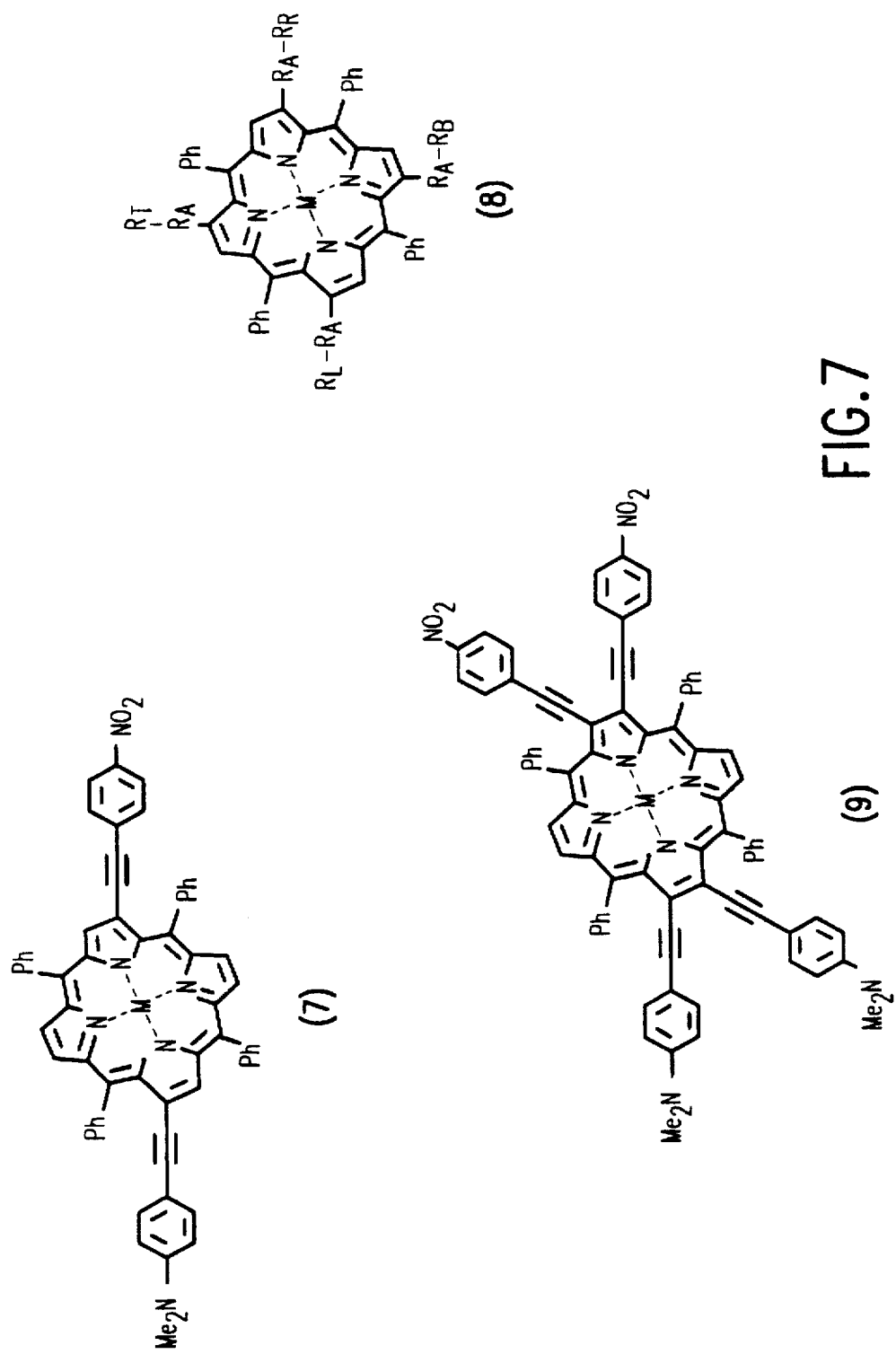
FIGS. 7–10 show representative compounds according to the invention.
Figure 8:
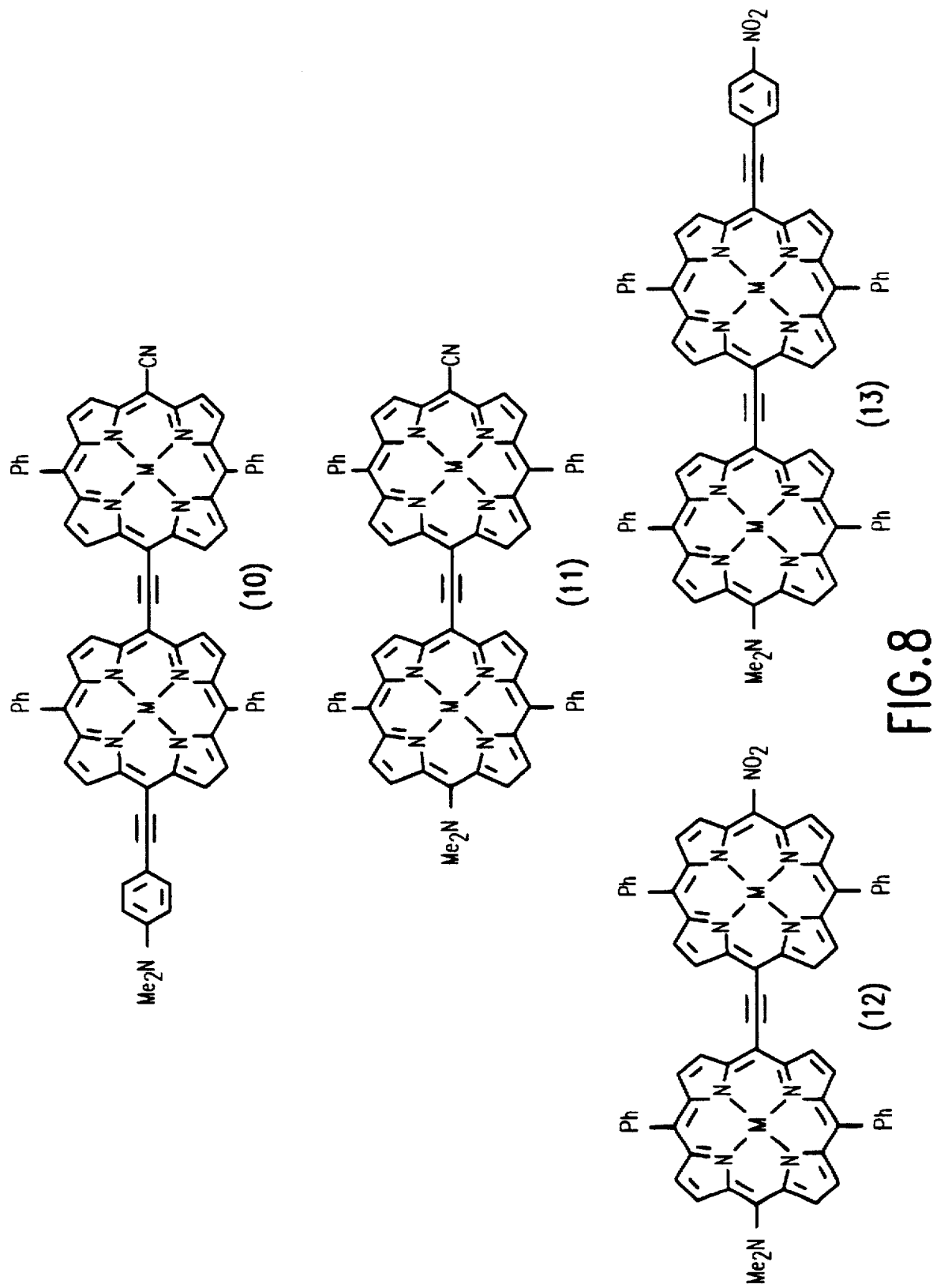
Figure 9:
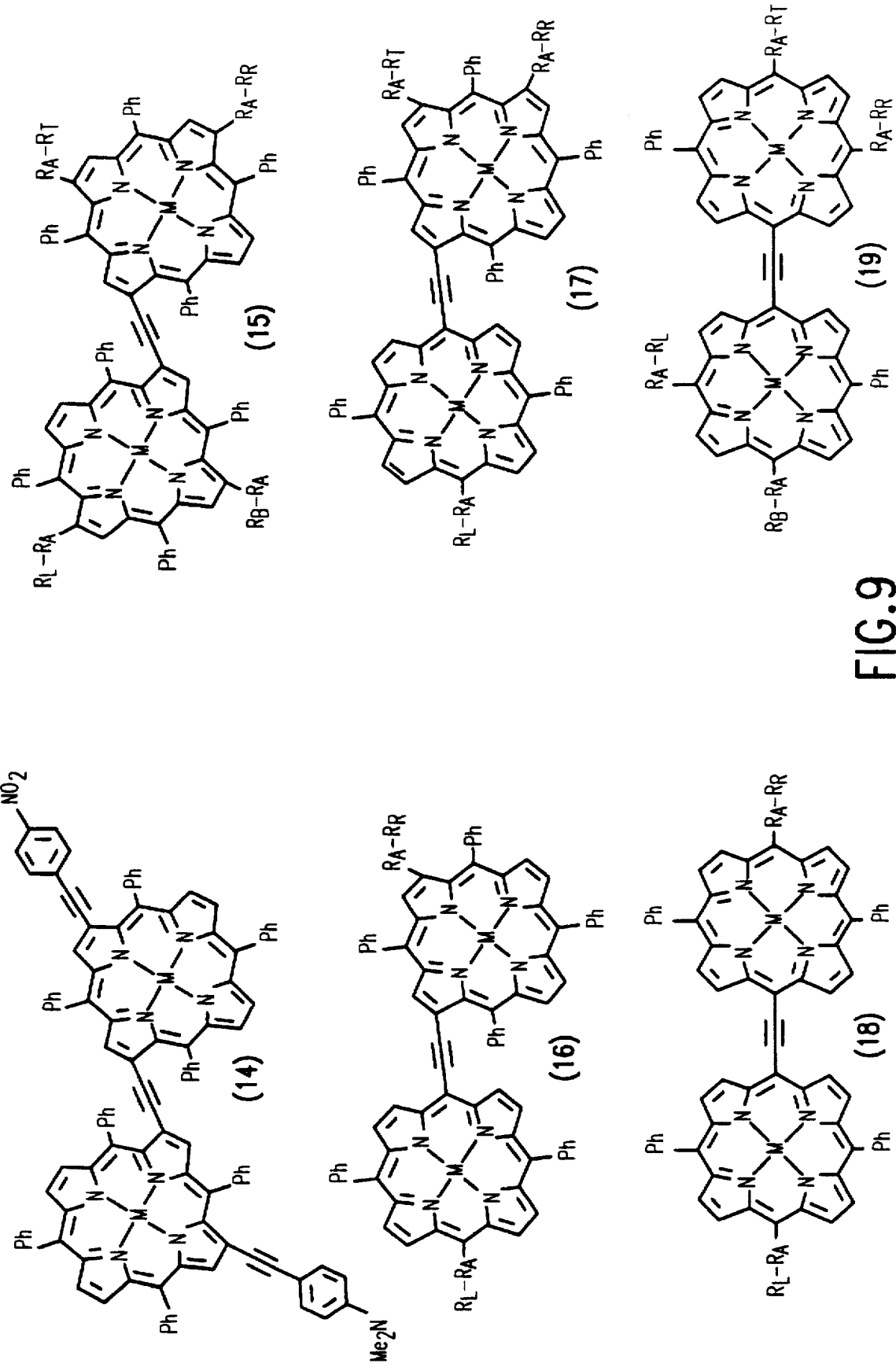
Figure 10:
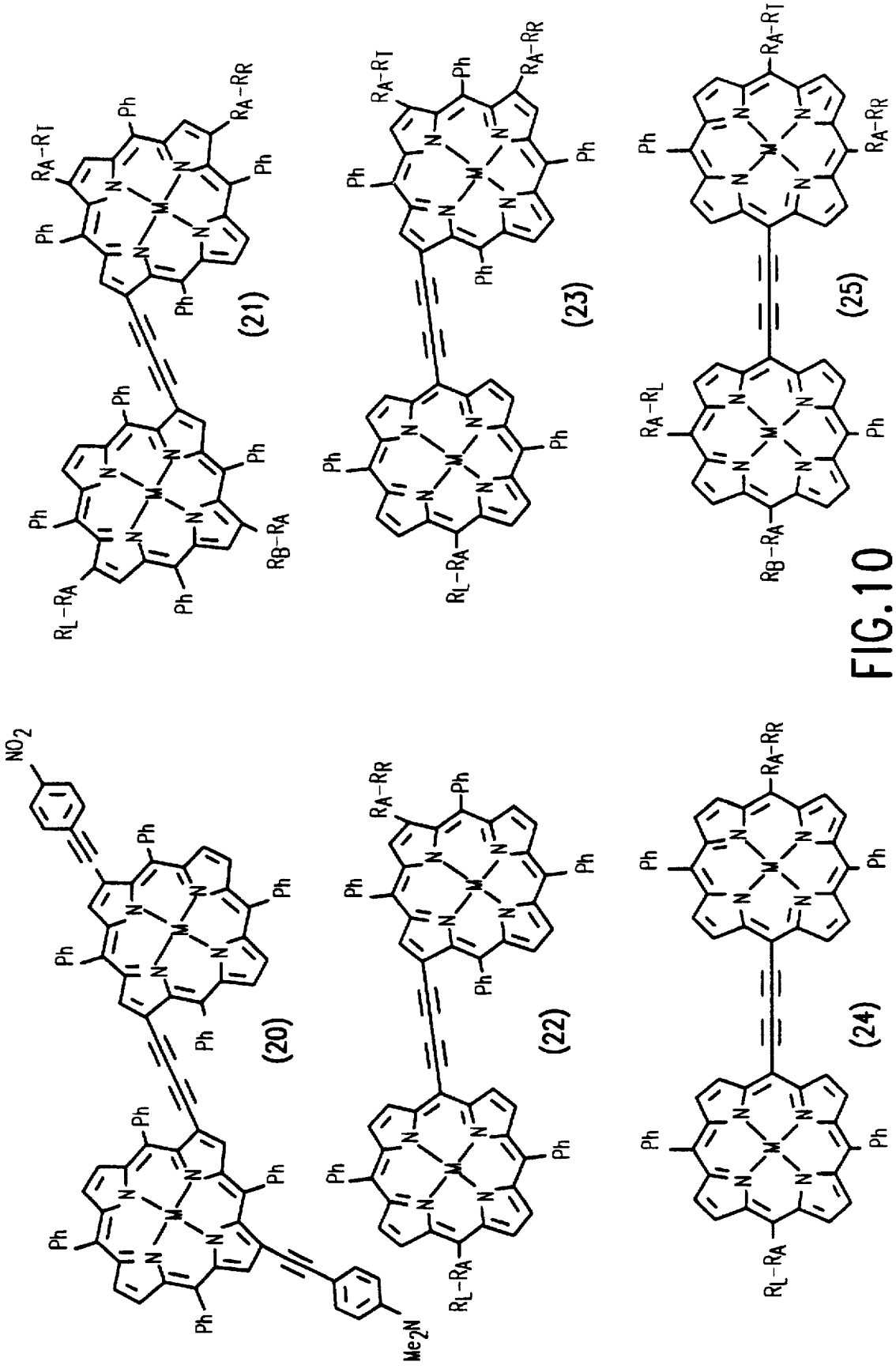

As shown in FIG. 6, devices according to the invention generally comprise a dielectric or some other substrate 10 and a layer 12, disposed on the substrate, comprising at least one compound of the invention. Useful substrates include semiconductors such as silicon or gallium arsenide or insulators such as glass or plastic. Layer 12 can contain a compound of the invention in polymeric form. Those skilled in the art will recognize that a wide variety of polymers can be prepared using the compounds of the invention. In certain embodiments, cofacial polymers such as those disclosed in U.S. Pat. No. 5,371,199 can be used.

In other embodiments, the chromophores of the invention can be incorporated into the backbone of the polymer. Representative structures are those in which linear polymer chains are formed wherein a portion of the polymer has general formula $[MC]_r$ where r is at least 2. In further embodiments, linear polymer chains have general formula:

where $Q_L$ is a linking group and h, l, and s are independently selected to be at least 1. Representative examples of such polymers can have formula:

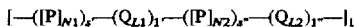

wherein $[P]_{N1}$ and $[P]_{N2}$ are independently selected porphyrins or extended π-macrocycles. $Q_{L1}$ and $Q_{L2}$ are independently selected linking groups, and 1', 1", s', and s" are at least 1. These essentially linear polymer chains can be cross-linked such that a portion of the polymer has general formula:

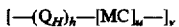

wherein $Q_H$ is a linking group, and h, u, and v are independently selected to be at least 1. Representative examples of these cross-linked polymers can have formula:

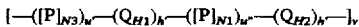

wherein $[P]_{N3}$ is a porphyrin, $Q_{H1}$ and $Q_{H2}$ are independently selected linking groups, and h', h", u', and u" are at least 1. Thus, cross-linked polymers can have formulas:

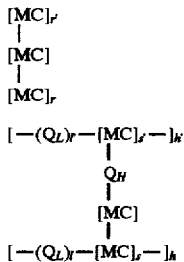

where r' is at least 1.

The polymers of the invention can be formed by contacting a substituted compound with a second compound containing functionality that is reactive with the functionality contained within the substituted compound. Preferably, one of the compounds contains an olefinic carbon-carbon double bond, a carbon-carbon triple bond, or some other reactive functionality such as an amine, acid, aldehyde or ester. The contacting should be performed under conditions effective to form a covalent bond between the respective reactive functionalities. Preferably, porphyrin-containing polymers are formed by metal-mediated cross-coupling of, for example, dibrominated porphyrin units. Also, polymers of the invention can be synthesized using known terminal alkyne coupling chemistry. (see, e.g., Patai, et al., The Chemistry of Functional Groups, Supplement C, Part 1, pp. 529–534, Wiley, 1983; Cadiot, et al., Acetylenes, pp. 597–647, Marcel Dekker, 1964; and Eglinton, et al., Adv. Org. Chem., 1963, 4, 225) As will be recognized, the second compound noted above can be a substituted porphyrin of the invention or some other moiety such as an acrylate monomer. Thus, a wide variety of copolymeric structures can be synthesized with the compounds of the invention. Through careful substituent selection the porphyrins of the invention can be incorporated into virtually any polymeric matrix known in the art, including but not limited to polyimides, polymethacrylates, polyacrylates, polyacetylenes, polyolefins, polyethers, polyurethanes, polycarbonates, polyanilines, polypyrroles, and polythiophenes. For example, fluorescent porphyrins can be incorporated into such polymers as end-capping groups.

Alteratively, layer 12 can contain a compound of the invention in combination with one or more synthetic organic polymers. In certain embodiments, for example, the layer can include synthetic organic polymer or precursors thereof (e.g., monomers, catalysts, and sensitizers) in admixture with a compound of the invention. Such embodiments offer the possibility of effecting cross-linking and/or in situ polymerization following mixture of the polymer or polymer precursor system with a compound of the invention. Where the polymer constitutes a major proportion of the layer and the compound constitutes a minor proportion of the layer, the compound can be said to be a "guest" in the "host" polymer.

It is believed that the compounds of the invention can be mixed with many synthetic organic polymers and polymer precursor systems known in the art. In some instances, it may be desirable to adapt the a compound of the invention to include functional groups that improve the compound's solubility in a polymer or precursor of interest. It is also believed that the compounds of the invention can be covalently bound with an equally wide variety of polymers, possibly through use of linking moieties such as alkyl, alkoxyl, and or alkylamino groups. Representative synthetic organic polymers include polyimides, polyacrylates, polymethacrylates, polyesters, polycarbonates, polystyrenes, polyolefins, and polyvinyl ethers. Polyimides and other transparent polymers having high $T_g$ are preferred.

The coating of a substrate with a material comprising a compound of the invention can be accomplished by any means known in the art, preferably by spin-coating, role-coating, or physical vapor deposition. L. I. Maissel and R. Glang, Handbook of Thin Film Technology, McGraw-Hill (1970); Satas, Coating Technology Handbook, Marcel Dekker (1991). The materials used to form layer 12 can further include other moieties such as, for example, pigments, dyes, filters and dopants.

Polymerization and/or crosslinking of a layer following its deposition on a substrate can be accomplished in any of the ways known to those skilled in the art. For example, certain polymerizations can be effected by simple heating in the presence of a suitable initiator or by the incidence of light or some other form of electromagnetic energy in the presence or absence of a sensitizer. The latter procedure is preferred due to the ability of those in the art to effect selective, patterned polymerization through the use of, for example, removable masking agents. As will be recognized, devices incorporating appropriately arrayed patterns of polymer can be employed in microcircuitry and other applications.

In embodiments such as shown in FIG. 6, certain devices of the invention comprise a conductor superstrate 14 disposed on layer 12, control means 16, and contacts 18 attached to substrate 10 and superstrate 14. This arrangement allows an input light signal 20 from source 22 to be operated upon by virtue of a changing electric field within layer 12 generated by control means 16 in concert with contacts 18. Altered or "operated" light signal 24 is directed away from the layer to a suitable detector 26. A wide variety of devices fitting this general description are well-known to those skilled in the art. Representative examples are disclosed by Burland, et al., Chem. Rev. 1994, 94, 31.

Additional objects, advantages, and novel features of this invention will become apparent to those skilled in the art upon examination of the following examples thereof, which are not intended to be limiting.

EXAMPLE 1

Synthesis of [5-[[4'-(Dimethylamino)phenyl] ethynyl]-15-bromo-10,20-diphenylporphinato]zinc(II)

(5,15-Dibromo-10,20-diphenylporphinato)zinc(II) (252 mg, 369 μmol), CuI (10 mg, 52 μmol), Pd[PPh₃]₄ (35 mg, 30 μmol), diethylamine (5 ml), THF (30 ml), and p-dimethylaminophenylacetylene were brought together in a 100 ml Schlenk tube under an N₂ atmosphere. The resulting solution becomes intensely green as the reaction precedes at room temperature. At the reaction endpoint (t=12 h), the crude product was purified by column chromatography on silica gel using 4:1 hexanes:THF as eluant. The green band was collected and evaporated to give a deep green (almost black) residue (97.5 mg, 35 percent).

EXAMPLE 2

Synthesis of [5-(4'-Dimethylaminophenylethynyl)-15-(4"-nitrophenylethynyl)-10,20-diphenyiporphinato]zinc(II) ("1(Zn")")

[5-[[4'-(Dimethylamino)phenyl]ethynyl]-15-bromo-10, 20-diphenylporphinato]zinc(II) (52.0 mg, 102 μmol), p-nitrophenylacetylene (35.2 mg, 240 μmol), Pd[PPh₃]₄ (15.0 mg, 13 μmol), and copper(I) iodide (6-6 mg, 35 μmol) were placed in a 50 ml Schlenk tube under an N₂ atmosphere. Tetrahydrofuran (10 ml) and diethylamine (1 ml) were added. The reaction vessel was shielded from light and allowed to react at room temperature. After 12 hours, the solution was evaporated to dryness and the solid purified by column chromatography (silica gel, 3:1 hexanes:THF). The green band was collected and dried to give the desired product (57.0 mg, 97 percent). ¹H NMR (250 MHz, CDCl₃, d₅-Pyridine): δ 9.63 (d, 2H,J=4.6), 9.51 (d, 2H, J=4.6),8.78 (d, 2H, J=4.6),8.73 (d, 2H, J=4.6),8.10 (m, 6 H, 7.83 (d, 2 H, J=8.7), 7.75 (d, 2 H, J=8.9), 7.64 (m, 6 H), 6.69 (d, 2 H, J=8.8),2.93 (s, 6 H. ¹³CNMR (60 MHz, CDCl3, d₅-pyridine) δ 152.06, 151.46, 150.08, 149.93, 146.13, 142.40, 134.25, 132.66, 132.55, 131.94, 131.31, 131.11, 130.79, 129.84, 127.23, 126.29, 123.60, 122.73, 111.82, 110.49, 104.14, 99.67, 98.58, 97.52, 94.11, 91.23. Vis (THF): 460 (5.27), 678 (4.88). FAB MS: 812.19 (calc'd 812.19). Anal. Calc'd for C₅₄H₄₀N₆O₃ZnC₄H₈(THF): C, 73.18; H, 4.55; N, 9.48. Found: C, 73.04; H, 4.48; N, 9.40.

EXAMPLE 3

Synthesis of [5-[[4'-(dimethylamino)phenyl]ethynyl] -15-[(4"-nitrophenyl)ethynyl]-10,20-diphenylporphinato]copper(II) ("1 (Cu")")

Analytically pure [5-[[4'-(dimethylamino)phenyl] ethynyl]-15-[(4"-nitrophenyl)ethynyl]-10,20-diphenylporphinato]zinc(II) (20.6 mg, 25.3 μmol) was dissolved in 50 ml of a 1:1 THF:CHCl₃ solution in a 125 ml Erlenmeyer flask. Concentrated hydrochloric acid (0.5 ml) was added dropwise. After 5 minutes, triethylamine (5 ml) was added. The mixture was stirred an additional 5 minutes before being placed into a 125 ml separatory funnel. The organic layer was washed once with 1.0M KOH (20 ml) and then with distilled water. The aqueous fractions were discarded and the organic layer rotary evaporated to dryness. The free base push-pull arylethynylporphyrin was used without further purification. Vis (THF): 446, 624, 708.

The 5-[[4'-(dimethylamino)phenyl]ethynyl]-15-[(4"-nitrophenyl)ethynyl]-10,20-diphenylporphyrin was placed in a 200 ml round bottom flask equipped with a stir bar. Toluene (60 ml) and cupric acetate•H₂O (100 mg, 501 mmol) were added. The resulting mixture was heated to reflux. After 6 hours, the mixture was cooled and placed in a 125 ml separatory funnel. The toluene layer was washed once with a 1M ammonium hydroxide solution (50 ml) and then twice with water (50 ml). The toluene layer was rotary evaporated to a total volume of approximately 15 ml and then chromatographed on silica gel using toluene as eluent. A tight, single green band was rotary evaporated to dryness and further dried under high vacuum to give 1(Cu") (12.0 mg, 58 percent based on 20.6 mg of compound 1(Zn")). Vis (THF): 452 (4.86), 656 (4.41). Low resolution FAB MS: 812 (calc'd 811).

EXAMPLE 4

Synthesis of Dibromothiasapphyrin (Formula (5) wherein R'=R"=Br)

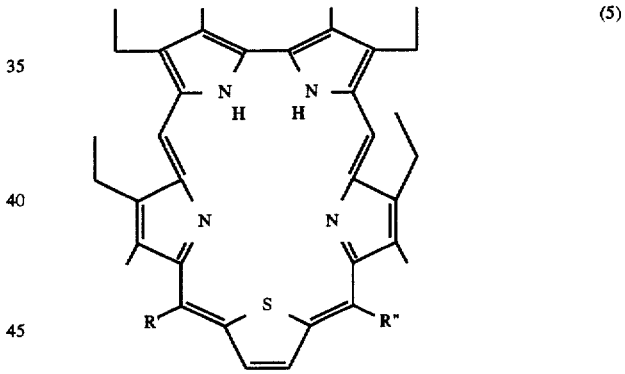

(5)

3,7,18,22-Tetraethyl-2,8,17,23-tetramethyl-27-thiasapphyrin ("thiasapphyrin"; 112 mg, 200 μmol; See, Sessler, et al., Tetrahedron 1992, 48, 9661) is dissolved in 100 ml of methylene chloride and is reacted with 2 eq. of N-bromosuccinimide at 0° C. for one hour. The reaction is quenched with 1 ml of triethylamine, the volatiles are removed, and the reaction is chromatographed to provide the title compound.

EXAMPLE 5

Synthesis of A Thiasapphyrin-based Chromophore (Formula (5) wherein R=[p-(dimethylamino) phenyl]acetylenyl and R"=(p-nitrophenyl)acetylenyl Dibromothiasapphyrin (100 mg, 139 μmol), CuI (4 mg, 21 μmol), Pd[PPh₃]₄ (12 mg, 10 μmol), diethylamine (5 ml) and [p-(dimethylamino)phenyl]acetylene (24.7 mg, 170 μmol) are brought together along with 20 ml of tetrahydrofuran in a 50 ml Schlenk tube under a nitrogen atmosphere. At the reaction endpoint, the crude product is purified by column chromatography.

The isolated material (50 mg, 64 μmol) is combined with (p-nitrophenyl)acetylene (51 mg, 350 μmol), Pd[PPh₃]₄ (7.5 mg, 6.5 μmol) and CuI (3.3 mg, 18 μmol) in a 50 ml Schlenk flask along with 10 ml of tetrahydrofuran and 1 ml of diethylamine. At the reaction endpoint, the product is purified by column chromatography.

EXAMPLE 6

Synthesis of 2-[[(4'-Dimethylamino)phenyl]ethynyl] -12-bromophthalocyanato]zinc(II)

(2,12-Dibromophthalocyanato)zinc(II) (221 mg, 300 μmol), CuI (10 mg, 52 μmol), Pd[PPh₃]₄ (35 mg, 30 μmol), diethylamine (5 ml), tetrahydrofuran (30 ml) and [p-(dimethylamino)phenyl]acetylene are brought together under N₂ in a 100 ml Schlenk tube. After 12 hours, the crude product is purified by column chromatography on silica gel to provide the title compound.

EXAMPLE 7

Synthesis of 2-[[(4'-Dimethylamino)phenyl]ethynyl] -12-[(4"-nitrophenylethynyl]phthalocyanato]zinc(II) (Formula (6))

A Nd:YAG laser (10 Hz; 3–8 ns pulse width) and a ti-sapphire laser (Coherent, Mira Model 9000; 76 MHz; 100 fs pulse width) were used as excitation sources. The intensity of the incident beam from the Nd:YAG laser, after it was filtered by a long pass filter to remove the second harmonic component as 0.53 μm, was varied by a combination of a polarizer and a half wave plate. The incident beam was focused onto the sample with a f/10 lens and the scattered light was collected by a f/1.3 lens followed by a bi-convex lens with a focal lens of 30 cm. The collected signal was directed to a photomultiplier tube with an interference filter and a sharp bandpass filter set at the second harmonic frequency attached in the front. A boxcar integrator was used to process the signal when the Nd:YAG was used as an excitation source. To take advantage of its high repetition rate, a photon counting system was utilized to process the light scattering signal when the Ti-sapphire laser was used as an excitation source. All HRS experiments were carried out at room temperature. The scattering angle was 90°. FIG. 3 shows the electronic absorption spectra of 1(Zn$^{II}$) and 1(Cu$^{II}$). Arrows at 532 and 415 nm indicate the wavelengths corresponding to the second harmonic of the fundamental incident 1064 and 830 nm irradiation respectively. FIGS. 4 and 5 plot the hyper Rayleigh scattering signal at I(2ω) versus chromophore number density for 1(Zn$^{II}$) and 1(Cu$^{II}$)

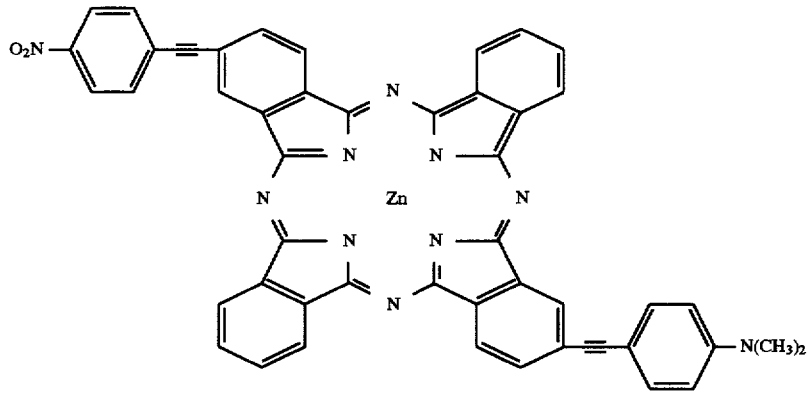

(6)

2-[[(4'-Dimethylamino)phenyl]ethynyl]-12-bromophthalocyanato]zinc(II) (80 mg, 100 μmol), p-(nitrophenyl)acetylene (35 mg, 240 μmol), Pd[PPh₃]₄ (15 mg, 13 μmol), and copper (I) iodide (6.6 mg, 35 μmol) are placed in a 50 ml Schlenk tube under N₂. Tetrahydrofuran (10 ml) and diethylamine (1 ml) are added. The reaction mixture is stirred at room temperature for 24 hours. The volatiles are removed in vacuo and the remaining solid is purified by column chromatography on silica gel.

EXAMPLE 8

Measurement of Molecular First Order Hyperpolarizability

Measurement of molecular first hyperpolarizability for 1 (Zn$^{II}$) and 1(Cu$^{II}$) was carried out in chloroform solvent for incident irradiation wavelengths of 830 ($\lambda_1$) and 1064 ($\lambda_2$) nm generally according to Pauley, et al., *J. Chem. Phys.* 1995, 102, 6400. All chromophores were dissolved in chloroform and filtered through 0.2 μm membrane to remove dust and any adventitious particulates. Successive dilution form a concentrated standard was utilized to prepare samples differing in chromophore concentration. Glass cuvettes (3.5 ml) were used as cells to hold the solution for the HRS experiment.

in chloroform solvent in the very dilute concentration regime for irradiation at wavelengths $\lambda_1$ and $\lambda_2$. (Internal reference: CHCl₃ solvent: $\beta_{(Chloroform)}$=−0.49×10$^{-30}$ esu; External reference: p-nitroaniline (PNA) in CHCl₃: $\beta_{(PNA)}$=23×10$^{-30}$ esu at 1.06 μm (HRS); $\beta$(PNA)=25×10$^{-30}$ esu at 1.06 μm (EFISH)). The solid lines in the figures represent the best fit to the data points. The quantities ($\rho_s$, $\beta_s$) and ($\rho_c$, $\beta_c$) denote the concentration and hyperpolarizabilty of solvent molecules and chromophores, respectively.

EXAMPLE 9

Preparation of Thin Films

Using a syringe, a nearly saturated solution of 1(Cu$^{II}$) is dispensed into LQ2200 polyimide resin (Hitachi Chemical) to make a 4% solution (dye/polymer weight ratio). The resulting solution is agitated slightly and then spin coated onto a glass-slide substrate, which is baked at 110° C. in a vacuum oven for one hour, cured at 200° C. for half an hour, and finally cured at 250° C. and above. The porphyrin-based guest molecules are aligned by application of a DC field on a coplanar electrode in the host polyimide. The resulting clear, green or blue/green film is about 2–4 μm thick. The thickness of the film can be controlled by adjusting the spin speed.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A compound having formula:

wherein:
- each [MC], independently, is a porphyrin, chlorin, phorbin, benzoporphyrin, bacteriochlorin, porphyrinogen, sapphyrin, texaphyrin, or phthalocyanine;
- each $R_A$, independently, is a covalent bond, alkenyl having 2 to about 20 carbon atoms, cumulenyl having 4 to about 14 carbon atoms, or alkynyl having 2 to about 10 carbon atoms, provided that at least one of $R_A$ is alkenyl, cumulenyl, or alkynyl;
- each $R_M$, independently, is alkyl having 1 to about 20 carbon atoms, alkenyl having 2 to about 20 carbon atoms, cumulenyl having 4 to about 14 carbon atoms, alkynyl having 2 to about 10 carbon atoms, aryl having 3 to about 50 carbon atoms, arylalkynyl having 10 to about 24 carbon atoms, or thioether having 1 to about 10 carbon atoms;
- one of $R_1$ and $R_2$ is a chemical group that is electron-donating;
- the other of $R_1$ and $R_2$ is a chemical group that is electron-withdrawing;
- m is 0 to about 50; and
- z is 0 or 1.

2. The compound of claim 1 wherein said electron-donating group is an alkyl group, an alkylamino group, an arylamino group, $NH_2$, an alkoxyl group, OH, an alkylthio group, SH, —OC(O)-(alkyl), a cycloheptatriene, or a heterocycle.

3. The compound of claim 1 wherein said electron-withdrawing group is haloalkyl, N-(alkyl)$_3^+$, S-(alkyl)$_2^+$, $NH_3^+$, $NO_2$, $SO_2$-(alkyl), CN, $SO_2$-(aryl), C(O)OH, F, Cl, Br, I, cyclopentadienyl, C(O)O-(alkyl), C(O)-(alkyl), CHO, or a heterocycle.

4. The compound of claim 1 having formula:

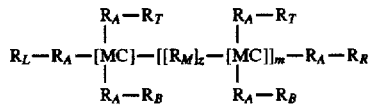

wherein each $R_L$, $R_T$, $R_R$, and $R_B$ is, independently, an electron-donating group or an electron-withdrawing group, provided that at least one of $R_L$, $R_T$, $R_R$, and $R_B$ is an electron-donating group and at least one of $R_L$, $R_T$, $R_R$, and $R_B$ is an electron-withdrawing group.

5. The compound of claim 4 wherein:
- one pair of $R_L$ and $R_T$, $R_L$ and $R_B$, $R_R$ and $R_T$, or $R_R$ and $R_B$ are chemical groups that are electron-donating; and
- the other pair of $R_L$ and $R_T$, $R_L$ and $R_B$, $R_R$ and $R_T$, and $R_R$ and $R_B$ is a chemical group that is electron-withdrawing.

6. The compound of claim 1 having formula (1) or (2):

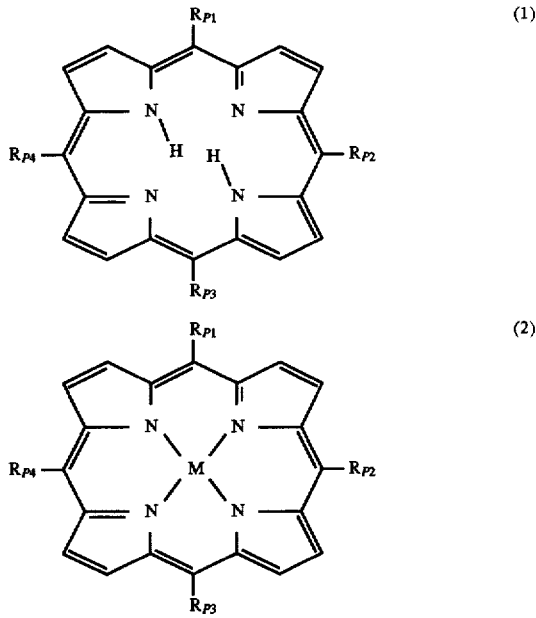

wherein:
- M is a metal atom;
- $R_{P1}$ is —$R_A$, —$R_T$ or aryl having 3 to about 60 carbon atoms;
- $R_{P2}$ is —$R_A$, —$R_R$;
- $R_{P3}$ is —$R_A$, —$R_B$ or aryl having 3 to about 60 carbon atoms;
- $R_{P4}$ is —$R_A$, —$R_L$;
- $R_A$, is a covalent bond, cumulenyl, polyenyl, or polyynyl; and
- each $R_L$, $R_T$, $R_R$, and $R_B$ is, independently, an electron-donating group or an electron-withdrawing group, provided that at least one of $R_L$, $R_T$, $R_R$, and $R_B$ is an electron-donating group and at least one of $R_L$, $R_T$, $R_R$, and $R_B$ is an electron-withdrawing group.

7. The compound of claim 1 having formula (3) or (4):

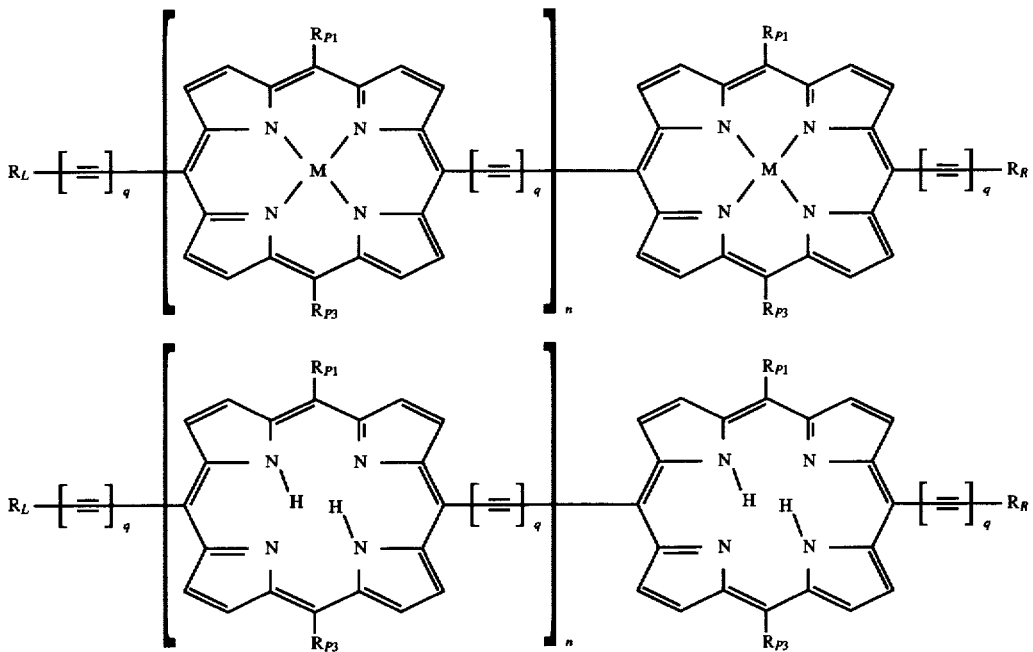

wherein:

M is a metal atom;

$R_{P1}$ is —$R_A$, —$R_T$ or aryl having 3 to about 60 carbon atoms;

$R_{P3}$ is —$R_A$, —$R_B$ or aryl having 3 to about 60 carbon atoms;

$R_A$, is a covalent bond, cumulenyl, polyenyl, or polyynyl;

each $R_L$, $R_T$, $R_R$, and $R_B$ is, independently, an electron-donating group or an electron-withdrawing group, provided that at least one of $R_L$, $R_T$, $R_R$, and $R_B$ is an electron-donating group and at least one of $R_L$, $R_T$, $R_R$, and $R_B$ is an electron-withdrawing group; and q is 1–5 and n is 0–50.

8. The compound of claim 7 wherein:

one pair of $R_L$ and $R_T$, $R_L$ and $R_B$, $R_R$ and $R_T$, and $R_R$ and $R_B$ are electron-donating chemical groups; and the other pair of $R_L$ and $R_T$, $R_L$ and $R_B$, $R_R$ and $R_T$, and $R_R$ and $R_B$ is an electron-withdrawing chemical group.

9. The compound of claim 7 wherein said electron-donating group is an aromatic hydrocarbon bearing at least one electron-donating substituent or a heterocycle bearing at least one electron-donating substituent.

10. The compound of claim 9 wherein said electron-donating substituent is an alkyl group, an alkylamino group, an arylamino group, $NH_2$, an alkoxyl group, OH, an alkylthio group, SH, or —OC(O)-(alkyl).

11. The compound of claim 7 wherein said electron-withdrawing group is an aromatic hydrocarbon bearing at least one electron-withdrawing substituent or a heterocycle bearing at least one electron-withdrawing substituent.

12. The compound of claim 11 wherein said electron-withdrawing substituent is haloalkyl, N-(alkyl)$_3^+$, S-(alkyl)$_2^+$, $NH_3^+$, $NO_2$, $SO_2$-(alkyl), CN, $SO_2$-(aryl), C(O)OH, F, Cl, Br, I, C(O)O-(alkyl), C(O)-(alkyl) or CHO.

13. The compound of claim 7 wherein said electron-donating group is 4-dimethylaminophenyl or julolidinyl.

14. The compound of claim 7 wherein said electron-withdrawing group is 4-nitrophenyl, 4-cyanophenyl, N,N'-diethylthiobarbituric acid, or 3-phenyl-5-isoxazolone.

15. The compound of claim 1 having a β value greater than 500×10$^{-30}$ esu at 1906 nm or 1064 nm incident radiation.

16. The compound of claim 1 that is [5-[[4'-(dimethylamino)phenyl]ethynyl]-15-[(4"-nitrophenyl)ethynyl]-10,20-diphenylporphinato]zinc(II).

17. The compound of claim 1 that is [5-[[4'-(dimethylamino)phenyl]ethynyl]-15-[(4"-nitrophenyl)ethynyl]-10,20-diphenylporphinato]copper(II).

18. A device comprising a substrate and at least one layer on said substrate, said layer including a compound according to claim 1.

19. The device of claim 18 further comprising a superstrate on said layer.

20. The device of claim 18 further comprising means for establishing an electric field across said layer.

21. The device of claim 18 further comprising sensing means for detecting light transmitted by said layer.

22. A composition comprising synthetic organic polymer and at least one compound according to claim 1.

23. The composition of claim 22 wherein said polymer is in admixture with said compound.

24. The composition of claim 22 wherein said polymer is covalently bound with said compound.

25. The composition of claim 22 wherein said polymer constitutes a major proportion of said composition and said compound constitutes a minor proportion of said composition.

26. The composition of claim 22 wherein said polymer is a polyimide, a polyacrylate, a polymethacrylate, a polyester, a polycarbonate, a polystyrene, a polyolefin, a polyvinyl ether, or a mixture thereof.

27. A process for preparing a device, comprising the steps of:

providing a substrate; and placing upon said substrate at least one layer that includes a compound according to claim 1.

* * * * *